(12) United States Patent
Adams et al.

(10) Patent No.: US 6,632,614 B2
(45) Date of Patent: *Oct. 14, 2003

(54) **METHOD FOR DETECTING ANTI-*STREPTOCOCCUS PYOGENES* DNASE B ANTIBODY IN A TEST SAMPLE**

(75) Inventors: Craig W. Adams, Corona, CA (US); Patty P. Y. Pang, Rancho Cucamonga, CA (US); C. Marina Belei, Anaheim, CA (US)

(73) Assignee: Beckman Coulter, Inc., Fullerton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,900

(22) Filed: Jul. 21, 1998

(65) Prior Publication Data

US 2002/0081622 A1 Jun. 27, 2002

Related U.S. Application Data

(62) Division of application No. 08/472,630, filed on Jun. 7, 1995, which is a division of application No. 08/393,889, filed on Feb. 24, 1995, now Pat. No. 6,420,152, which is a continuation of application No. 08/082,845, filed on Jun. 23, 1993, now abandoned.

(51) Int. Cl.[7] .............................................. G01N 33/53
(52) U.S. Cl. ...................... 435/7.1; 435/7.32; 435/7.34; 435/7.94; 435/7.95; 435/18; 435/19; 435/195; 435/196; 436/517; 436/518; 436/536
(58) Field of Search ............................ 435/4, 7.1, 7.32, 435/7.34, 7.91, 7.92, 7.94, 68.1, 69.1, 69.2, 18, 19, 195, 196; 436/517, 524, 529, 532, 536, 543, 518

(56) References Cited

U.S. PATENT DOCUMENTS

| | | | |
|---|---|---|---|
| 3,793,149 A | | 2/1974 | Blank et al. |
| 3,920,625 A | | 11/1975 | Anderson et al. |
| 4,421,650 A | * | 12/1983 | Nagasawa et al. .......... 210/635 |
| 4,481,291 A | | 11/1984 | Gils |
| 4,503,035 A | | 3/1985 | Pestka et al. |
| 4,658,017 A | | 4/1987 | Dembinski et al. |
| 4,832,849 A | * | 5/1989 | Cardin ....................... 210/635 |
| 5,055,395 A | | 10/1991 | Toth |
| 5,082,785 A | | 1/1992 | Manning et al. |

FOREIGN PATENT DOCUMENTS

EP          0613947          9/1994

OTHER PUBLICATIONS

Dwivedy Indian J Med Res 88=475–479, 1988.*
Collet–Cassant et al (Clin Chem, 35C1) : 141–143, 1989.*
Whiche et al, Nephelometric Methods in "Practical Immunoassay" Butt et al eds, NY. Marcel Dekker Inc. pp. 117–177, 1984.*
Davis et al "Microbiology", 1980, Harper & Row, p. 608, 1980.*
M.A. Gerber et al., "Enzyme–Linked Immunosorbent . . . DNase B," J. Lab. Clin. Med. 95:258–265 (1980).
T. Yutsudo et al. "A New Type of . . . *Streptococcus pyogenes*," FEBS Lett. 308:30–34 (1992).
M. Iwasaki et al., "Cloning, Characterization and . . . Mitogenic Factor," FEBS Lett. 331:187–192 (1993).
J. Sambrook et al., "Molecular Cloning, A Laboratory Manual" (Cold Spring Harbor Laboratory Press, Cold Spring Harbor, New York, 1989), chs. 11–12 and 17.
J.M. Wozney, "Using Purified Protein to Clone Its Gene," Methods Enzymol. 182:738–749 (1990).
G.Sofer, "Chromatographic Removal of Pyrogens," Bio/Technology: 1035–1038 (1984).
G.C. Klein & W.L. Jones, "Comparison of the . . . Tests," Appl. Microbiol. 21:257–259 (1971).
S. Horinouchi et al., "A New Isolation . . . *Achromobacter lyticus*," Agric. Biol. Chem. 41:2487–2489 (1977).
R.A. Young & R.W. Davis, "Efficient Isolation . . . Probes," Proc. Natl. Acad. Sci. USA 80:1194–1198 (1983).
J.E. Mott et al., "Maximizing Gene Expression . . . Factor D," Proc. Natl. Acad. Sci. USA 82:88–92 (1985).
E.D. Sevier et al., "Monoclonal Antibodies in Clinical Immunology," Clin. Chem. 27:1797–1805 (1981).
E. L. V. Harris et al., "Protein Purification Methods: A Practical Approach", IRL Press, 1989, pp 56–65.
R. Lathe, "Synthetic Oligonucleotide Probes Deduced from Amino Acid Sequence Data: Theoretical and practical Considerations", Journal of Molecular biology, vol. 183, No. 1, May 5, 1985, pp. 1–11.
Tavernier et al., "Effects of Divalent Cations on Activity and Specificity of Streptococcal Nucleases B and D", Biochemistry, vol. 9, No. 14, 1970, pp. 2846–2852.
T. Waldström et al., "Preparative Scale Purification of Bacterial Enzymes and Toxins by Isoelectric Focusing and Isotachophoresis", Proceedings of the International Symposium on Electrofocusing and Isotachohoresis, 1976 1977, pp. 443–453.
W. G. Yasminch, "Streptococcal Nucleases. V. Specificities of Deoxyribonuclease Action of the A.B.C. and D Enzymes", Biochemistry, vol. 7, No. 1, Jan. 1968, pp. 105–113.

* cited by examiner

Primary Examiner—Patricia A. Duffy
(74) Attorney, Agent, or Firm—Gates & Cooper; William H. May; D. David Hill

(57) ABSTRACT

The gene for *Streptococcus pyogenes* DNase B has been cloned and vectors incorporating the cloned DNA have been used to transform *Escherichia coli*, allowing efficient and rapid production of the DNase in *E. coli* without the necessity of growing large quantities of *S. pyogenes*. The enzyme can be produced with a leader peptide at its amino terminus. An improved method for the purification of naturally occurring *S. pyogenes* DNase B enzyme is also provided. The DNase B enzyme produced, either by purification of naturally occurring enzyme or by recombinant DNA techniques, can be used to generate antibodies and can also be used in immunochemical assays to detect the presence of anti-DNase B antibodies in serum as a marker of infection by *S. pyogenes*.

19 Claims, 14 Drawing Sheets

FIG. 3A (SEQ ID NO: 8, 9)

Figure 1:
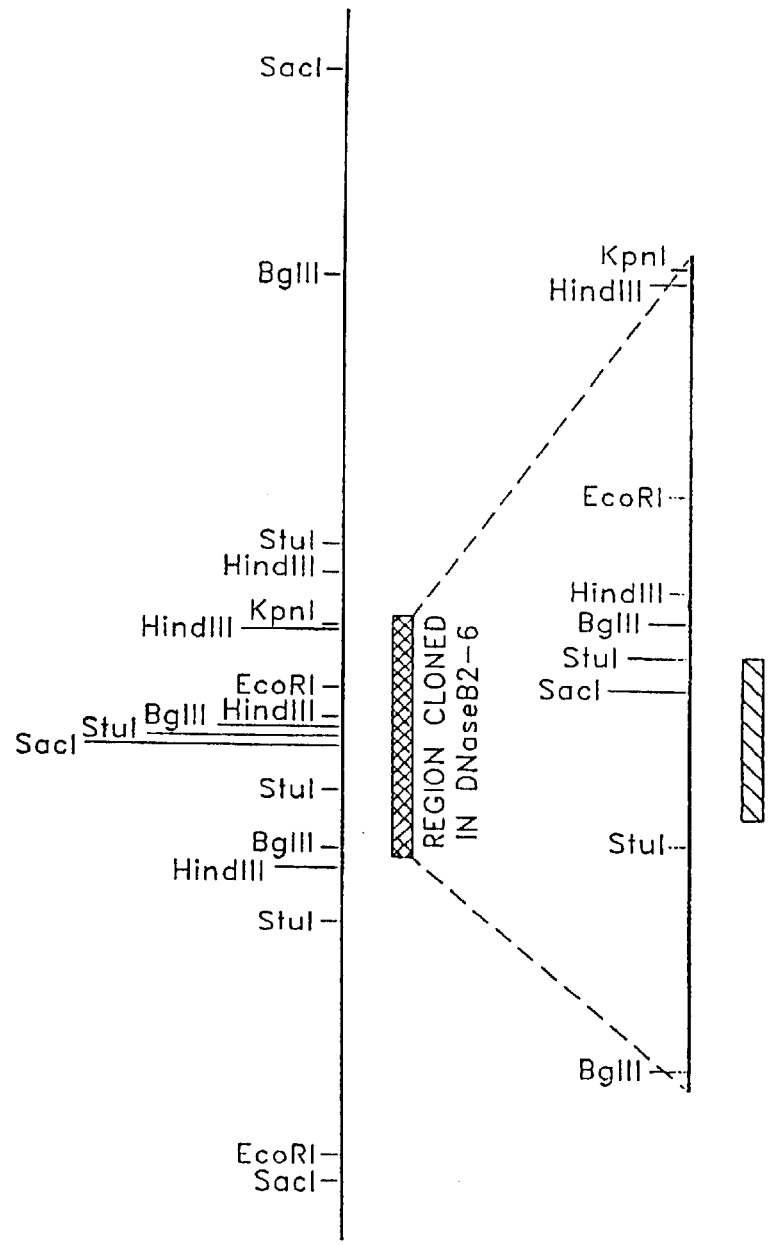

```
                                    T
                              M     s                  MD                    SM   M                 AX
                              s     p                  sr                    pa   s                 cc
                              e     E                  ea                    ee   e                 ca
                              I     I                  II                    II   I                 II

GACAACGCCTTCTTTTTTCTCCTTACTATCTCCTTTAATTTTCATATTTTTTAAAAAAACTATTGATAAACTAGTTAAGTAAGCGTATACTATGGTTAGT
  1 ---------+---------+---------+---------+---------+---------+---------+---------+---------+---------+ 100
    CTGTTGCGGAAGAAAAAAGAGGAATGATACAGGAAATTAAAAGTATAAAAAATTTTTTTGATAACTATTTGATCAATTCATTCGCATATGATACCAATCA a:                                                                                                       -
b:                                                                                                       -
c:                                                                                                       -

T
                                           t
                                           h     S
                                           1     a
          T                       H        1 u D              A                         C       T         C
         sM                      A i       1 3 p              l                        vM       s        Av
         pn                      d n       I A n              w                        is       p        li
         El                      e f       I   I              I                        Je       E        uJ
         II                      I I       III                                         II       I        II

TAGCGAAATTAGAAAAGAGGACAAGCATATGAATCTACTTGGATCAAGACGGGTTTTTTCTAAAAAATGTCGGCTAGTAAAATTTTCAATGGTAGCTCTT
101 ---------+---------+---------+---------+---------+---------+---------+---------+---------+---------+ 200
    ATCGCTTTAATCTTTTCTCCTGTTCGTATACTTAGATGAACCTAGTTCTGCCCAAAAAAGATTTTTTACAGCCGATCATTTTAAAAGTTACCATCGAGAA a:                                                                                                       -
b:                                                                                                       -
c:                     MetAsnLeuLeuGlySerArgArgValPheSerLysLysCysArgLeuValLysPheSerMetValAlaLeu -

T
                                                                             t
                          M         M T                                     EUh                  H
          C              a         a s                                      cbl                  i
          v      B       v e       e p              B                       oal                n H
          i      g       i I       I 4              s                       321                P h
          J      l       J I       I 5              r                       16I                l a
          I      I       I I       I I              I                       III                I I GTATCAGCCACAATGGCTGTAACAACAGTCACACTTGAAAATACTGCACTGGCACGACAAACACAGGTCTCAAATGATGTTGTTCTAAATGATGGCGCAA
201 ---------+---------+---------+---------+---------+---------+---------+---------+---------+---------+ 300
    CATAGTCGGTGTTACCGACATTGTTGTCAGTGTGAACTTTTATGACGTGACCGTGCTGTTTGTGTCCAGAGTTTACTACAACAAGATTTACTACCGCGTT a:                                                                                                       -
b:                                                                                                       -
c: ValSerAlaThrMetAlaValThrThrValThrLeuGluAsnThrAlaLeuAlaArgGlnThrGlnValSerAsnAspValValLeuAsnAspGlyAlaSer -

T
                 t
                 h
          C      1       C                                     C                                 E
         vR      1      Av                                    GvRMS                              c
         is      1      li                                    sissp                              o
         Qa      I      uJ                                    uQaee                              N
         II      I      II                                    IIIII                              I GCAAGTACCTAAACGAAGCATTAGCTTGGACATTCAATGACAGTCCTAACTATTACAAAACTTTAGGTACTAGTCAGATTACTCCAGCACTCTTTCCTAA
301 ---------+---------+---------+---------+---------+---------+---------+---------+---------+---------+ 400
    CGTTCATGGATTTGCTTCGTAATCGAACCTGTAAGTTACTGTCAGGATTGATAATGTTTTGAAATCCATGATCAGTCTAATGAGGTCGTGAGAAAGGATT a:                                                                                                       -
b:                                                                                                       -
c: LysTyrLeuAsnGluAlaLeuAlaTrpThrPheAsnAspSerProAsnTyrTyrLysThrLeuGlyThrSerGlnIleThrProAlaLeuPheProLys -
```

FIG. 3B

```
                              A
                              f
                  T           1MT   vMRH  M    vR                    C
                  s           Ilh   insg  a    is                    Av
                  p           Iua   Qlaa  e    Qa                    li
                  E           III   IIII  I    II                    uJ
                  I                                                  II
                                    / //         /                   /
        AGCAGGAGATATTCTCTATAGCAAATTAGATGAGTTAGGAAGGACGCGTACTGCTAGAGGTACATTGACTTATGCCAATGTTGAAGGTAGCTACGGTGTT
   401  ----------+---------+---------+---------+---------+---------+---------+---------+---------+---------+  500
        TCGTCCTCTATAAGAGATATCGTTTAATCTACTCAATCCTTCCTGCGCATGACGATCTCCATGTAACTGAATACGGTTACAACTTCCATCGATGCCACAA a:                                                                                                              -
b:                                                                                                              -
c:      AlaGlyAspIleLeuTyrSerLysLeuAspGluLeuGlyArgThrArgThrAlaArgGlyThrLeuThrTyrAlaAsnValGluGlySerTyrGlyVal     -
```

```
                                          N
                                          l                  T
                                  B  F    a         s        MH
                                  s  o    I         p        as
                                  r  k    I         E        eo
                                  I  I    I         I        II
        AGACAATCTTTCGGTAAAAATCAAAACCCCGCAGGATGGACTGGAAACCCTAATCATGTCAAATATAAAATTGAATGGTTAAATGGTCTATCTTATGTCG
   501  ----------+---------+---------+---------+---------+---------+---------+---------+---------+---------+  600
        TCTGTTAGAAAGCCATTTTTAGTTTTGGGGCGTCCTACCTGACCTTTGGGATTAGTACAGTTTATATTTTAACTTACCAATTTACCAGATAGAATACAGC a:                                                                                                              -
b:                                                                                                              -
c:      ArgGlnSerPheGlyLysAsnGlnAsnProAlaGlyTrpThrGlyAsnProAsnHisValLysTyrLysIleGluTrpLeuAsnGlyLeuSerTyrValGly -
```

```
                            U        B
                    S       b        c         H          M          A
                    f       a        e  D      i          a          f  M    C
                    a       2        f  d      n          P e        l  s    vR       M
                    n       6        I  e      f          e I        I  e    is       n
                    I       I        X  I      I          I I        II II   Qa       l
                                                                                 /    I
        GAGATTTCTGGAATAGAAGTCATCTCATTGCAGATAGTCTCGGTGGAGATGCACTCAGAGTCAATGCCGTTACAGGAACACGTACCCAAAATGTAGGAGG
   601  ----------+---------+---------+---------+---------+---------+---------+---------+---------+---------+  700
        CTCTAAAGACCTTATCTTCAGTAGAGTAACGTCTATCAGAGCCACCTCTACGTGAGTCTCAGTTACGGCAATGTCCTTGTGCATGGGTTTTACATCCTCC a:                                                                                                              -
b:                                                                                                              -
c:      AspPheTrpAsnArgSerHisLeuIleAlaAspSerLeuGlyGlyAspAlaLeuArgValAsnAlaValThrGlyThrArgThrGlnAsnValGlyGly   -
```

```
                                             B
                                             s
          M T           F    HM               p
          a s                il N            CB1H                       C
          e p           n    naMsS           Ava2gS                     v
          I 4           u    PIhpp           lin81a                     i
          I 5           4    1IaHH           uJI6Ac                     J
          I I           H    IIIII           IIIII                      I
                        I
                                  / //             / ///
        TCGTGACCAAAAAGGCGGCATGCGCTATACCGAACAAAGAGCTCAAGAATGGTTAGAAGCAAATCGTGATGGCTATCTTTATTATGAAGTCGCTCCAATC
   701  ----------+---------+---------+---------+---------+---------+---------+---------+---------+---------+  800
        AGCACTGGTTTTTCCGCCGTACGCGATATGGCTTGTTTCTCGAGTTCTTACCAATGTTCGTTTAGCACTACCGATAGAAATAATACTTCAGCGAGGTTAG a:                                                                                                              -
b:                                                                                                              -
c:      ArgAspGlnLysGlyGlyMetArgTyrThrGluGlnArgAlaGlnGluTrpLeuGluAlaAsnArgAspGlyTyrLeuTyrTyrGluValAlaProIle  -
```

FIG. 3C

```
      H         C                    M                                                      C
      i         Av                   b                                                      Av
      n         li                   o                                                      li
      f         uJ                   I                                                      uJ
      I         II                                                                          II
                /                    /                                                      /
      TACAACGCAGACGAGTTGATTCCAAGAGCTGTCGTGGTATCAATGCAATCTTCTGATAATACCATCAACGAGAAAGTATTAGTTTACAACACAGCTAATG
801   ---------+---------+---------+---------+---------+---------+---------+---------+---------+---------+ 900
      ATGTTGCGTCTGCTCAACTAAGGTTCTCGACAGCACCATAGTTACGTTAGAAGACTATTATGGTAGTTGCTCTTTCATAATCAAATGTTGTGTCGATTAC a:                                                                                                        -
b:                                                                                                        -
c:    TyrAsnAlaAspGluLeuIleProArgAlaValValValSerMetGlnSerSerAspAsnThrIleAsnGluLysValLeuValTyrAsnThrAlaAsnGly -
```

```
                                                                                     M
      C                    C                        C                        C   s   C
      v        M           vR                       vH                       MM  vMaMSAv
      i        s           is                       ia                       an  isIstli
      J        e           Qa                       Jc                       el  JeIeuuJ
      I        I           II                       II                       II  IIIIIII
                           /                                                  / ////  /
      GCTACACCATTAACTACCATAACGGTACACCTACTCAAAAATAATACCAAAAGGCTAGACCTCTGCTCACTAGGCCTAGCTTTTTACATCAAAAAAAGCA
901   ---------+---------+---------+---------+---------+---------+---------+---------+---------+---------+ 1000
      CGATGTGGTAATTGATGGTATTGCCATGTGGATGAGTTTTTATTATGGTTTTCCGATCTGGAGACGAGTGATCCGGATCGAAAAATGTAGTTTTTTTCGT a:                                                                                                        -
b:                                                                                                        -
c:    TyrThrIleAsnTyrHisAsnGlyThrProThrGlnLysEnd
```

```
                      B
                      c
          M           e                                            T
          s           f                                            s
          e           I                                            p
          I           X                                            E
                                                                   I
      ATGACTATAGAAAGTAAAAATACTAGAAAAAGCAATGATTGCCGTCATTGCTTTTTATGAATTTGTGCAAAAAGCAAAAAAGC
1001  ---------+---------+---------+---------+---------+---------+---------+---------+--- 1083
      TACTGATATCTTTCATTTTTATGATCTTTTTCGTTACTAACGGCAGTAACGAAAAATACTTAAACACGTTTTTCGTTTTTTCG a:                                                             MetAsnLeuCysLysLysGlnLysSer -
b:                                                                                         -
c:    MetIleAlaValIleAlaPheTyrGluPheValGlnLysAlaLysLys???                                   -
```

ENZYMES THAT DO CUT:

| AccI | AflIII | AluI | AlwI | BanII | BceflX | BglI | Bsp1286I | BsrI | CviJI | CviQI | DdeI | DpnI |
|---|---|---|---|---|---|---|---|---|---|---|---|---|
| DraI | Eco31I | EcoNI | Fnu4HI | FokI | SsuI | MaeI | MaeIII | HgaI | HgiAI | HhaI | HinfI | HinP1I |
| MseI | MaeII | MseIII | MboII | MluI | MmeI | MnlI | MseI | MdeI | MlaIII | HspAI | PleI | RsaI |
| SacI | Sau3AI | SfaNI | SpeI | SphI | StuI | ThaI | Tsp45I | TspEI | Tth111I | Uba26I | XcaI | |

ENZYMES THAT DO NOT CUT:

| AatII | AflII | AhaII | AlwNI | AocI | ApaI | ApaII | Asp700I | Asp718I | AsuII | AvaI | AvaII | AvrII |
|---|---|---|---|---|---|---|---|---|---|---|---|---|
| BalI | BamHI | BanI | BbeI | BbvI | BbvII | BclI | BglII | BsmI | BspHI | BspMI | BspMII | BssHI |
| BstEII | BstHI | BstXI | CfrI | Cfr10I | ClaI | DraII | DraIII | DsaI | Eco47III | Eco57I | Eco78I | EcoRI |
| EcoRII | EcoRV | EspI | FinI | FinI | FspI | GdiII | HaeIII | HgiEII | HincII | HindIII | HpaIO | HpaII |
| MphI | KpnI | Ksp632I | MfeI | HaeI | MarI | NciI | NcoI | NheI | NlaII | NotI | NruI | NsiI |
| Msp6II | PflMI | PmaCI | PpuMI | PssI | PstI | PvuI | PvuII | RsrII | SacII | SalI | Sau96I | ScaI |
| SciI | ScrfI | SeaI | SfiI | SmaI | SmaII | SplI | SsoII | SspI | StyI | TaqI | TaqII | TaqII |
| Tth111I | VspI | XbaI | XhoI | XhoII | XmaI | XmaIII | | | | | | |

AMINO ACID SEQUENCE OF CLONED S. PYOGENES DNase

R-Q-T-Q-V-S-N-D-V-V-L-N-D-G-A-S-K-Y-L-N-
E-A-L-A-W-T-F-N-D-S-P-N-Y-Y-K-T-L-G-T-S-
Q-I-T-P-A-L-F-P-K-A-G-D-I-L-Y-S-K-L-D-E-
L-G-R-T-R-T-A-R-G-T-L-T-Y-A-N-V-E-G-S-Y-
G-V-R-Q-S-F-G-K-N-Q-N-P-A-G-W-T-G-N-P-N-
H-V-K-Y-K-I-E-W-L-N-G-L-S-Y-V-G-D-F-W-N-
R-S-H-L-I-A-D-S-L-G-G-D-A-L-R-V-N-A-V-T-
G-T-R-T-Q-N-V-G-G-R-D-Q-K-G-G-M-R-Y-T-E-
Q-R-A-Q-E-W-L-E-A-N-R-D-G-Y-L-Y-Y-E-V-A-
P-I-Y-N-A-D-E-L-I-P-R-A-V-V-V-S-M-Q-S-S-
D-N-T-I-N-E-K-V-L-V-Y-N-T-A-N-G-Y-T-I-N-
Y-H-N-G-T-P-T-Q-K (SEQ ID NO: 9)

*FIG. 4*

PCR OLIGONUCLEOTIDE

5' TAACGGATCCGAATCTACTTGGATCAAGACGGGTTTTTTCT 3' (SEQ. ID NO: 2)

```
      ATGGATCCGAATCTACTTGGATCAAGACGGGTTTTTCTAAAAAATGTCGGCTAGTAAAA
  1   ------------+---------+---------+---------+---------+---------+ 60
      TACCTAGGCTTAGATGAACCTAGTTCTGCCCAAAAAAGATTTTTTACAGCCGATCATTTT
      MetAspProAsnLeuLeuGlySerArgArgValPheSerLysLysCysArgLeuValLys

TTTTCAATGGTAGCTCTTGTATCAGCCACAATGGCTGTAACAACAGTCACACTTGAAAAT
 61   ------------+---------+---------+---------+---------+---------+ 120
      AAAAGTTACCATCGAGAACATAGTCGGTGTTACCGACATTGTTGTCAGTGTGAACTTTTA
      PheSerMetValAlaLeuValSerAlaThrMetAlaValThrThrValThrLeuGluAsn

ACTGCACTGGCACGACAAACACAGGTCTCAAATGATGTTGTTCTAAATGATGGCGCAAGC
121   ------------+---------+---------+---------+---------+---------+ 180
      TGACGTGACCGTGCTGTTTGTGTCCAGAGTTTACTACAACAAGATTTACTACCGCGTTCG
      ThrAlaLeuAlaArgGlnThrGlnValSerAsnAspValValLeuAsnAspGlyAlaSer

AAGTACCTAAAACGAAGCATTAGCTTGGACATTCAATGACAGTCCTAACTATTACAAAACT
181   ------------+---------+---------+---------+---------+---------+ 240
      TTCATGGATTTGCTTCGTAATCGAACCTGTAAGTTACTGTCAGGATTGATAATGTTTTGA
      LysTyrLeuAsnGluAlaLeuAlaTrpThrPheAsnAspSerProAsnTyrTyrLysThr

TTAGGTACTAGTCAGATTACTCCAGCACTCTTTCCTAAAGCAGGAGATATTCTCTATAGC
241   ------------+---------+---------+---------+---------+---------+ 300
      AATCCATGATCAGTCTAATGAGGTCGTGAGAAAGGATTTCGTCCTCTATAAGAGATATCG
      LeuGlyThrSerGlnIleThrProAlaLeuPheProLysAlaGlyAspIleLeuTyrSer

AAATTAGATGAGTTAGGAAGGACGCGTACTGCTAGAGGTACATTGACTTATGCCAATGTT
301   ------------+---------+---------+---------+---------+---------+ 360
      TTTAATCTACTCAATCCTTCCTGCGCATGACGATCTCCATGTAACTGAATACGGTTACAA
      LysLeuAspGluLeuGlyArgThrArgThrAlaArgGlyThrLeuThrTyrAlaAsnVal

GAAGGTAGCTACGGTGTTAGACAATCTTTCGGTAAAAATCAAAACCCCGCAGGATGGACT
361   ------------+---------+---------+---------+---------+---------+ 420
      CTTCCATCGATGCCACAATCTGTTAGAAAGCCATTTTTAGTTTTGGGGCGTCCTACCTGA
      GluGlySerTyrGlyValArgGlnSerPheGlyLysAsnGlnAsnProAlaGlyTrpThr

GGAAACCCTAATCATGTCAAATATAAAATTGAATGGTTAAATGGTCTATCTTATGTCGGA
421   ------------+---------+---------+---------+---------+---------+ 480
      CCTTTGGGATTAGTACAGTTTATATTTTAACTTACCAATTTACCAGATAGAATACAGCCT
      GlyAsnProAsnHisValLysTyrLysIleGluTrpLeuAsnGlyLeuSerTyrValGly
```

*FIG. 5A*

```
        GATTTCTGGAATAGAAGTCATCTCATTGCAGATAGTCTCGGTGGAGATGCACTCAGAGTC
481     ---------+---------+---------+---------+---------+---------+ 540
        CTAAAGACCTTATCTTCAGTAGAGTAACGTCTATCAGAGCCACCTCTACGTGAGTCTCAG

AspPheTrpAsnArgSerHisLeuIleAlaAspSerLeuGlyGlyAspAlaLeuArgVal

AATGCCGTTACAGGAACACGTACCCAAAATGTAGGAGGTCGTGACCAAAAAGGCGGCATG
541     ---------+---------+---------+---------+---------+---------+ 600
        TTACGGCAATGTCCTTGTGCATGGGTTTTACATCCTCCAGCACTGGTTTTTCCGCCGTAC

AsnAlaValThrGlyThrArgThrGlnAsnValGlyGlyArgAspGlnLysGlyGlyMet

CGCTATACCGAACAAAGAGCTCAAGAATGGTTAGAAGCAAATCGTGATGGCTATCTTTAT
601     ---------+---------+---------+---------+---------+---------+ 660
        GCGATATGGCTTGTTTCTCGAGTTCTTACCAATCTTCGTTTAGCACTACCGATAGAAATA

ArgTyrThrGluGlnArgAlaGlnGluTrpLeuGluAlaAsnArgAspGlyTyrLeuTyr

TATGAAGTCGCTCCAATCTACAACGCAGACGAGTTGATTCCAAGAGCTGTCGTGGTATCA
661     ---------+---------+---------+---------+---------+---------+ 720
        ATACTTCAGCGAGGTTAGATGTTGCGTCTGCTCAACTAAGGTTCTCGACAGCACCATAGT

TyrGluValAlaProIleTyrAsnAlaAspGluLeuIleProArgAlaValValValSer

ATGCAATCTTCTGATAATACCATCAACGAGAAAGTATTAGTTTAGAACAGAGCTAATGGC
721     ---------+---------+---------+---------+---------+---------+ 780
        TACGTTAGAAGACTATTATGGTAGTTGCTCTTTCATAATCAAATGTTGTGTCGATTACCG

MetGlnSerSerAspAsnThrIleAsnGluLysValLeuValTyrAsnThrAlaAsnGly

TACACCATTAACTACCATAACGGTACACCTACTCAAAAATAATACCAAAAGGCTAGACCT
781     ---------+---------+---------+---------+---------+---------+ 840
        ATGTGGTAATTGATGGTATTGCCATGTGGATGAGTTTTTATTATGGTTTTCCGATCTGGA

TyrThrIleAsnTyrHisAsnGlyThrProThrGlnLysEndTyrGlnLysAlaArgPro

CTGCTCACTAGGCCTAGCTTTTTACATCAAAAAAAGCAATGACTATAGAAAGTAAAAATA
841     ---------+---------+---------+---------+---------+---------+ 900
        GACGAGTGATCCGGATCGAAAAATGTAGTTTTTTTCGTTACTGATATCTTTCATTTTTAT

LeuLeuThrArgProSerPheLeuHisGlnLysLysGlnEnd

CTAGAAAAAGCAATGATTGCCGTCATTGCCCCGGGTCGACCCGG
901     ---------+---------+---------+---------+---- 944   (SEQ. ID NO: 1)
        GATCTTTTTCGTTACTAACGGCAGTAACGGGGCCCAGCTGGGCC

3' TCTTTTTCGTTACTAACGGCAGTAACGGGGCCCAGCTGGGCC 5'   (SEQ. ID NO: 3)
           PCR OLIGONUCLEOTIDE
```

*FIG. 5B*

```
  1 GACAACGCCTTCTTCTTTTTCTCCTTACTATCTCCTTAATTTTCATATTTTTAAAAAAACTATTGATAAACTAGTAGTTAAGTAAGCGTATACTATGGTTAGT
                                                          -35                                          -10
101 TAGCGAAATTAGAAAAGAGGACAAGCATATGAATCTACTTGGATCAAGACGGGTTTTTCTAAAAAATGTCGGCTAGTAAAATTTTCAATGGTAGCTCTT
                                                                                              **
```

(SEQ. ID NO: 10)

CONSENSUS SEQUENCE OF *ESCHERICHIA COLI* PROMOTER REGION:

```
   -35         -10
tcTTGACat    TAtAaT
```

*FIG. 7*

SEQUENCE OF CONSTRUCTION PRODUCING DNASE B
PROCESSED IDENTICALLY TO NATURAL DNASE B

PCR OLIGONUCLEOTIDE (SEQ ID NO: 12

5'AGGCAATGGATCCGAACCTGCTGGGTTCCCGTCGTGTTTTCTCCAAAAAATGCCGTCTGGTTAAATTCTCCAT

```
        ATGGATCCGAACCTGCTGGGTTCCCGTCGTGTTTTCTCCAAAAAATGCCGTCTGGTTAAATTCTCCAT
     1  ---------+---------+---------+---------+---------+---------+  60
        TACCTAGGCTTAGATGAACCTAGTTCTGCCCAAAAAAGATTTTTTACAGCCGATCATTTTAAAAGTTA

MetAspProAsnLeuLeuGlySerArgArgValPheSerLysLysCysArgLeuValLysPheSerMet -

GGTTGCTCTGGTTTCCGCTACCATGGCTGTTACCACCGTTACCCTGGAAAACACCGCTCT
    61  ---------+---------+---------+---------+---------+---------+  120
        CCATCGAGACCATAGTCGGTGTTACCGACATTGTTGTCAGTGTGAACTTTTATGACGTGA

ValAlaLeuValSerAlaThrMetAlaValThrThrValThrLeuGluAsnThrAlaLeu -

GGCT***CAGACACAGGTCTCAAATGATGTTGTTGTAAATGATGGCGCAAGCTTCATGGA
        GGCT***CAGACACAGGTCTCAAATGATGTTGTTCTAAATGATGGCGCAAGCAAGTACCT
   121  ---------+---------+---------+---------+---------+---------+  180
        CCGTGCTGTTTCTCTCCAGAGTTTACTACAACAAGATTTACTACCGCGTTCGTTCATGGA

AlaArgGlnThrGlnValSerAsnAspValValLeuAsnAspGlyAlaSerLysTyrLeu -

AAACGAAGCATTAGCTTGGACATTCAATGACAGTCCTAACTATTACAAAACTTTAGGTAC
   181  ---------+---------+---------+---------+---------+---------+  240
        TTTGCTTCGTAATCGAACCTGTAAGTTACTGTCAGGATTGATAATGTTTTGAAATCCATG

AsnGluAlaLeuAlaTrpThrPheAsnAspSerProAsnTyrTyrLysThrLeuGlyThr -

TAGTCAGATTACTCCAGCACTCTTTCCTAAAGCAGGAGATATTCTCTATAGCAAATTAGA
   241  ---------+---------+---------+---------+---------+---------+  300
        ATCAGTCTAATGAGGTCGTGAGAAAGGATTTCGTCCTCTATAAGAGATATCGTTTAATCT

SerGlnIleThrProAlaLeuPheProLysAlaGlyAspIleLeuTyrSerLysLeuAsp -

TGAGTTAGGAAGGACGCGTACTGCTAGAGGTACATTGACTTATGCCAATGTTGAAGGTAG
   301  ---------+---------+---------+---------+---------+---------+  360
        ACTCAATCCTTCCTGCGCATGACGATCTCCATGTAACTGAATACGGTTACAACTTCCATC

GluLeuGlyArgThrArgThrAlaArgGlyThrLeuThrTyrAlaAsnValGluGlySer -

CTACGGTGTTAGACAATCTTTCGGTAAAAATCAAAACCCCGCAGGATGGACTGGAAACCC
   361  ---------+---------+---------+---------+---------+---------+  420
        GATGCCACAATCTGTTAGAAAGCCATTTTTAGTTTTGGGGCGTCCTACCTGACCTTTGGG

TyrGlyValArgGlnSerPheGlyLysAsnGlnAsnProAlaGlyTrpThrGlyAsnPro -

TAATCATGTCAAATATAAAATTGAATGGTTAAATGGTCTATCTTATGTCGGAGATTTCTG
   421  ---------+---------+---------+---------+---------+---------+  480
        ATTAGTACAGTTTATATTTTAACTTACCAATTTACCAGATAGAATACAGCCTCTAAAGAC

AsnHisValLysTyrLysIleGluTrpLeuAsnGlyLeuSerTyrValGlyAspPheTrp -

GAATAGAAGTCATCTCATTGCAGATAGTCTCGGTGGAGATGCACTCAGAGTCAATGCCGT
   481  ---------+---------+---------+---------+---------+---------+  540
        CTTATCTTCAGTAGAGTAACGTCTATCAGAGCCACCTCTACGTGAGTCTCAGTTACGGCA

AsnArgSerHisLeuIleAlaAspSerLeuGlyGlyAspAlaLeuArgValAsnAlaVal -
```

FIG. 10A

```
     TACAGGAACACGTACCCAAAATGTAGGAGGTCGTGACCAAAAAGGCGGCATGCGCTATAC
541  ------------+----------+----------+----------+----------+  600
     ATGTCCTTGTGCATGGGTTTTACATCCTCCAGCACTGGTTTTTCCGCCGTACGCGATATG

ThrGlyThrArgThrGlnAsnValGlyGlyArgAspGlnLysGlyGlyMetArgTyrThr -

CGAACAAAGAGCTCAAGAATGGTTAGAAGCAAATCGTGATGGCTATCTTTATTATGAAGT
601  ------------+----------+----------+----------+----------+  660
     GCTTGTTTCTCGAGTTCTTACCAATCTTCGTTTAGCACTACCGATAGAAATAATACTTCA

GluGlnArgAlaGlnGluTrpLeuGluAlaAsnArgAspGlyTyrLeuTyrTyrGluVal -

CGCTCCAATCTACAACGCAGACGAGTTGATTCCAAGAGCTGTCGTGGTATCAATGCAATC
661  ------------+----------+----------+----------+----------+  720
     GCGAGGTTAGATGTTGCGTCTGCTCAACTAAGGTTCTCGACAGCACCATAGTTACGTTAG

AlaProIleTyrAsnAlaAspGluLeuIleProArgAlaValValValSerMetGlnSer -

TTCTGATAATACCATCAACGAGAAAGTATTAGTTTACAACACAGCTAATGGCTACACCAT
721  ------------+----------+----------+----------+----------+  780
     AAGACTATTATGGTAGTTGCTCTTTCATAATCAAATGTTGTGTCGATTACCGATGTGGTA

SerAspAsnThrIleAsnGluLysValLeuValTyrAsnThrAlaAsnGlyTyrThrIle -

TAACTACCATAACGGTACACCTACTCAAAAATAATACCAAAAGGCTAGACCTCTGCTCAC
781  ------------+----------+----------+----------+----------+  840
     ATTGATGGTATTGCCATGTGGATGAGTTTTTATTATGGTTTTCCGATCTGGAGACGAGTG

AsnTyrHisAsnGlyThrProThrGlnLysEnd  (SEQ ID NO: 15)

TAGGCCTAGCTTTTTACATCAAAAAAAGCAATGACTATAGAAAGTAAAAATACTAGAAAA
841  ------------+----------+----------+----------+----------+  900
     ATCCGGATCGAAAAATGTAGTTTTTTTCGTTACTGATATCTTTCATTTTTATGATCTTTT

3' TCTTTT

AGCAATGATTGCCGTCATTGCCCCGGGTCGAC  (SEQ ID NO: 14)
901  ------------+----------+-------  936
     TCGTTACTAACGGCAGTAACGGGGCCCAGCTG

TCGTTACTAACGGCAGTAACGGGGCCCAGCTGGGCC 5'  (SEQ ID NO: 13)
       PCR OLIGONUCLEOTIDE
```

FIG. 10B

METHOD FOR DETECTING ANTI-*STREPTOCOCCUS PYOGENES* DNASE B ANTIBODY IN A TEST SAMPLE

This is a Divisional of application Ser. No. 08/472,630, filed Jun. 7, 1995, which in turn was a Divisional of application Ser. No. 08/393,889 (now U.S. Pat. No. 6,420,152), filed Feb. 24, 1995, which in turn was a file wrapper continuation application of application Ser. No, 08/082,845, filed Jun. 23, 1993 (now abandoned), which applications are incorporated herein by reference.

BACKGROUND OF THE INVENTION

This invention is directed to recombinant DNase B derived from the pathogenic bacterium *Streptococcus pyogenes*, methods for its production, and methods for its use.

Despite advances in the prevention and treatment of bacterial infection, a number of bacterial pathogens remain serious problems in medical practice and continue to cause severe, even fatal disease. One of these pathogens is *S. pyogenes*. Among the diseases caused by *S. pyogenes* are streptococcal pharyngitis ("strep throat"), scarlet fever, and their suppurative complications, including cervical adenitis, otitis media, mastoiditis, peritonsillar abscesses, meningitis, pneumonitis, pneumonia, puerperal sepsis, cellulitis of the skin, impetigo, lymphangitis, erysipelas, acute glomerulonephritis, and rheumatic fever.

Such infections often occur in hospitals (nosocomial infection), particularly in patients whose normal immune system functioning is suppressed. The latter category includes patients with AIDS, patients taking immunosuppressive drugs for cancer or to prevent transplant rejection, and patients having poor circulation, e.g., patients with diabetes.

Because these diseases require rapid and effective treatment to eradicate the suppurative lesions and prevent sequelae caused by immunological reactions to persisting suppurative lesions, prompt diagnosis of the presence of *S. pyogenes* is essential in patients in whom such infections are suspected. Failure to diagnose *S. pyogenes* promptly can greatly complicate treatment or even make it impossible.

Although detection methods for *S. pyogenes* are currently available, these methods have defects, particularly in clinical applications.

Among the methods of detection of *S. pyogenes* is the detection of the presence of antibodies against DNase B, a DNA-degrading enzyme produced by *S. pyogenes*. This enzyme, which is excreted from *S. pyogenes* during infection, initiates development of substantial titers of antibody in patients who go on to develop acute rheumatic fever and acute glomerulonephritis.

Although other serum-based diagnostic tests for these rheumatic fever and glomerulonephritis are available, including the detection of antibodies to streptolysin O, and to hyaluronidase, assays for anti-DNase B antibodies offer certain advantages, because DNase B is found among nearly all strains of group A beta-hemolytic streptococci, and because high DNase B titers are found in patients with infections of the skin and pharynx.

Although a number of commercially-available tests exist for the assay of anti-DNase B antibody, these tests have defects. As indicated above, an improved test is greatly needed.

The commercially-available tests fall into three categories: (1) a DNase B inhibition-based assay using the ability of the antibody to inhibit enzymatic activity; (2) a latex agglutination assay for antibody against a variety of *S. pyogenes* antigens; and (3) a turbidimetric inhibition assay. ELISA assays have also been used in the research laboratory, but, as detailed below, they have not yet proven suitable for routine clinical application.

The DNase B inhibition assay is very slow, and typically requires about 4–8 hours to perform. Thus, in situations in which confirmation of anti-DNase B antibody is required rapidly so the treatment can be started as soon as possible should the presence of *S. pyogenes* be confirmed, the enzyme inhibition assay is not particularly useful.

The latex agglutination assay is designed to detect antibodies to five *S. pyogenes* antigens. However, test results indicate poor agreement between the latex agglutination assay and a specific anti-DNase B tests. In one study, G. C. Klein & W. L. Jones, "Comparison of the Streptozyme Test with the Antistreptolysin O, Antideoxyribonuclease B, and Antihyaluronidase Tests," *App. Microbiol.* 21:257–259 (1971), 12 out of 80 patients that tested negatively in the latex agglutination assay were, in fact, positive for anti-DNase B antibody. This high level of false negative results means that the test is undesirable for clinical use.

The turbidimetric inhibition assay depends on the inhibition of agglutination of latex particles coated with anti-DNase B antibody by a limiting quantity of a crude preparation of DNase B in the presence of serum containing anti-DNase B antibody, which competes for the antibody on the latex particles. This assay, which is described in U.S. Pat. No. 5,055,395, incorporated herein by this reference, is relatively insensitive. Therefore, it is not suitable for use in the early stages of *S. pyogenes* infection, and it is precisely this period when accurate detection of the anti-DNase B antibody is most important. Additionally, the reagents used in the turbidimetric inhibition assay are difficult to manufacture.

ELISA-based assays for anti-DNase B antibody are reported in M. A. Gerber et al., "Enzyme-Linked Immunosorbent Assay of Antibodies in Human Sera to Streptococcal DNase B," *J. Lab. Clin. Med.* 95:258–265 (1980). Although these assays have proven effective as research tools, their scale-up for commercial use, particularly in clinical practice, has been impractical. This is because such scale-up would require production and purification of the DNase B enzyme of *Streptococcus pyogenes*, which is, as detailed above, a serious pathogen. Not only would extremely costly containment methods be required for growth of this pathogenic bacterium in the quantity required to produce sufficient enzyme for commercialization of the ELISA assay, the media required for the growth of *S. pyogenes* is very complex and expensive. These concerns have seriously hampered development of a commercial version of the ELISA assay for anti-DNase B antibody.

Therefore, there exists a need for an improved, rapid, and specific assay for anti-DNase B antibody. Preferably, such an assay would be usable by a physician in his office and would require minimal equipment. This is because patients with diseases such as strep throat or scarlet fever typically see their family physician prior to hospitalization, and accurate diagnosis of *S. pyogenes* infection at that point would be preferable to a subsequent diagnosis made only when the patient has been hospitalized.

The development of such an improved assay is dependent on the availability of large quantities of DNase B enzyme itself. Therefore, there is also a need for a method for the production of *S. pyogenes* DNase B enzyme using a procedure that can be scaled up to produce commercial quantities of the enzyme without requiring complex, unwieldy, and expensive containment measures.

SUMMARY

We have cloned and expressed the gene for *S. pyogenes* DNase B in *Escherichia coli*, allowing convenient and efficient production of the DNase B enzyme without requiring the growth of *S. pyogenes*.

This cloning procedure results in substantially purified DNA encoding an amino acid sequence selected from the group consisting of the amino acid sequence of: (i) *Streptococcus pyogenes* DNase B enzyme as shown in FIG. 4, below, which enzyme includes at its amino terminus an arginine (R) residue derived from a leader peptide and absent in the natural DNase B enzyme; and (ii) a sequence encoding a functional equivalent of *S. pyogenes* DNase B enzyme, optionally including at least one residue of the leader peptide. The DNA is substantially free of DNA other than DNA encoding the *S. pyogenes* DNase B sequence of FIG. 4, DNA encoding a functional equivalent of *S. pyogenes* DNase B enzyme, and DNA encoding the leader peptide.

Preferably, the DNA further comprises a DNA sequence coding for a leader peptide fused to the amino terminus of *S. pyogenes* DNase B enzyme.

Most preferably, the DNA cloned is the DNA whose sequence is given in FIG. 3, including the DNA coding for the entire amino acid sequence of *S. pyogenes* DNase B enzyme and the leader peptide.

Another aspect of the invention is expression vectors for *Streptococcus pyogenes* DNase B enzyme comprising the DNA sequences described above operatively linked to at least one control sequence compatible with a suitable bacterial host cell. Preferably, the expression vector is a plasmid vector. Typically, the DNA encoding the *Streptococcus pyogenes* DNase B enzyme is linked to at least one sequence from bacteriophage λ.

Another aspect of the invention is a bacterial host cell transformed, transfected, or infected with an expression vector according to the present invention in a manner allowing the transformed bacterial host cell to express the *Streptococcus pyogenes* DNase B encoded by the DNA incorporated within the expression vector in a detectable quantity. The expressed *S. pyogenes* DNase B can be either excreted or not excreted by the whole cell producing the enzyme, and can be in a soluble or an insoluble form.

Another aspect of the invention is substantially purified *S. pyogenes* DNAse B enzyme comprising a protein having the amino acid sequence of FIG. 4, or having an amino acid sequence substantially similar thereto.

Yet another aspect of the invention is a process for producing substantially purified *Streptococcus pyogenes* DNase B enzyme comprising:

(1) culturing the bacterial host cell transformed with an expression vector according to the present invention;

(2) using the cultured bacterial host cell to express the DNase B enzyme; and (3) purifying the enzyme from the cultured bacterial host cell.

Another aspect of the invention is *Streptococcus pyogenes* DNase B enzyme fused at its amino terminus with a leader peptide, the leader peptide having the sequence M-N-L-L-G-S-R-R-V-F-S-K-K-C-R-L-V-K-F-S-M-V-A-L-V-S-A-T-M-A-V-T-T-V-T-L-E-N-T-A-L-A-R (SEQ ID NO: 1).

Yet another aspect of the invention is a mutant of the protein whose amino acid sequence is shown in FIG. 4. In the mutant, at least one of the following mutations occurs:

(1) a deletion of one or more amino acids from the sequence of FIG. 4;

(2) an insertion of one or more naturally-occurring L-amino acids into the sequence of FIG. 4; and (3) replacement of at least one of the amino acids of FIG. 4 with an alternative naturally occurring L-amino acid. The resulting mutant has reduced or increased DNase B activity or another altered property. In one preferred alternative, the mutant substantially retains the antigenic reactivity of natural *S. pyogenes* DNase B enzyme.

Yet another aspect of the invention is the translational or transcriptional fusion of all or part of the *S. pyogenes* DNase B gene or protein to another gene or protein, with the resulting genetic construction having some altered property. These properties can include: (1) high level RNA expression; (2) high level protein expression; (3) a second functional enzyme, receptor, or other active protein in the fusion; (4) the fusion of the DNase B to an affinity ligand; (5) the production of a higher molecular weight protein; and (6) increased immunoreactivity.

Still another aspect of the invention is substantially purified natural *Streptococcus pyogenes* DNase B enzyme substantially free of proteins other than Streptococcus DNase B enzyme and Streptococcus DNase B enzyme fused at its amino terminus with a leader peptide. The substantially purified protein is substantially free of mitogenic activity. The substantially purified enzyme can be further purified into two fractions, Fraction I and Fraction II, depending on isoelectric point (pI). Each fraction can be purified into a preparation substantially free of the other fraction.

A process according to the invention for preparing substantially purified natural *S. pyogenes* DNase B enzyme can comprise:

(1) absorption to and elution from diethylaminoethyl cellulose to produce a first eluate;

(2) chromatography of the first eluate on phenyl agarose to produce a second eluate;

(3) chromatography of the second eluate on heparin agarose to produce a third eluate; and (4) chromatofocusing of the third eluate to produce substantially purified DNase B enzyme. Preferably, the process further comprises purification of the substantially purified DNase B by reverse-phase high-pressure liquid chromatography. The separation of Fractions I and II occurs at the chromatofocusing step as a consequence of the differing pI's of the enzymes of the two fractions.

Yet another aspect of the invention is a single-stranded nucleic acid probe hybridizing with at least about 17 nucleotides of the DNA sequence coding for the amino-terminal 23 amino acids of the *Streptococcus pyogenes* DNAse B enzyme, not including any portion of the leader sequence thereof, with no greater than about a 30% mismatch.

A further aspect of the present invention includes portions of the DNA sequence of sufficient size and specificity to serve as primer sites for amplification reactions such as polymerase chain reaction (PCR), ligase chain reaction (LCR), RCR, or other DNA amplification reactions. The same portions of the DNA sequence of *S. pyogenes* B can also serve as specific probes for detection of homologous sequences without DNA amplification.

The substantially purified *S. pyogenes* DNase B can be used to generate antibodies specifically binding the DNase B by techniques well known in the art. The antibodies can be either polyclonal or monoclonal.

Another aspect of the invention is a method for detecting and/or determining anti-*Streptococcus pyogenes* DNase B antibody in a test sample. The method comprises the steps of:

(1) providing a test sample suspected of containing anti-*Streptococcus pyogenes* DNase B antibody;

(2) adding a quantity of *Streptococcus pyogenes* DNase B enzyme according to the present invention to the test sample, the quantity being sufficient to produce a detectable level of enzymatic activity in the absence of inhibition of the enzymatic activity by anti-DNase B antibody in the test sample; and (3) determining a level of activity of DNase B enzyme in the test sample by performing an enzyme assay to detect and/or determine the anti-*Streptococcus pyogenes* antibody in the test sample.

An alternative method for detecting anti-DNase B antibody comprises the steps of:

(1) binding *Streptococcus pyogenes* DNase B enzyme according to the present invention to a solid support such as latex particles;

(2) reacting a test sample suspected of containing anti-*Streptococcus pyogenes* DNase B antibody with the *Streptococcus pyogenes* DNase B enzyme bound to the solid support to bind the antibody to the enzyme and thus to the solid support; and (3) detecting the antibody bound to the solid support to detect and/or determine the antibody in the test sample.

This approach can be used for nephelometric, turbidimetric, agglutination, or ELISA methods of quantitation.

An alternative method for detecting *S. pyogenes* DNase B antibody comprises:

(1) preparing a buffered solution of DNase B; (2) reacting the buffered DNase B solution with a test sample suspected of containing anti-*S. pyogenes* DNase B antibody; and (3) detecting a reaction between the DNase B and the anti-DNase B antibody by observing and/or measuring a change in light absorption and/or light scattering in the solution.

Another alternative method for detecting anti-DNase B antibody is capillary electrophoresis.

Because the cloned sequence includes a promoter associated with the *S. pyogenes* DNase B, gene, yet another aspect of the invention is a method of using the promoter originally associated with the *S. pyogenes* DNase B gene to express a protein other than DNase B. This method comprises:

(1) separating the promoter originally associated with the *S. pyogenes* DNase B gene from the *S. pyogenes* DNase B gene;

(2) operatively linking the promoter with a structural gene for a *S. pyogenes* protein other than the gene for DNase B; and (3) expressing the protein encoded by the structural gene.

The protein can be expressed in *S. pyogenes*, or in a prokaryote other than *S. pyogenes.*

Another aspect of the invention is a substantially purified promoter sequence derived from the promoter sequence originally associated with *S. pyogenes* DNase B including therein a start site for transcription and sites homologous to the consensus -10 and -35 sites of bacterial promoters.

Yet another aspect of the present invention is the use of the leader peptide of DNase B with the sequence M-N-L-L-G-S-R-R-V-F-S-K-K-C-R-L-V-K-F-S-M-V-A-L-V-S-A-T-M-A-V-T-T-V-T-L-E-N-T-A-L-A-R (SEQ ID NO: 1) to express a protein in a prokaryote. This aspect derives from the finding that when the entire cloned DNase B DNA segment, including the leader peptide, is expressed in *Escherichia coli*, the protein is excreted into the culture medium. A process for using the leader peptide to express a protein in a prokaryote comprises:

(1) fusing the DNA coding for the protein to DNA coding for the leader peptide so that the fused DNA codes for a recombinant protein with a single reading frame with the leader peptide being at the amino-terminus of the protein;

(2) introducing the fused DNA into the prokaryote; and (3) expressing the fused DNA in the prokaryote so that the recombinant protein is produced in a recoverable quantity.

The prokaryote can be *E. coli* or a gram-positive bacterium such as a Staphylococcus, Streptococcus, or Streptomyces species.

Another aspect of the present invention is a method for immunizing a mammal against infection with *S. pyogenes* comprising administering a quantity of purified *S. pyogenes* DNase B enzyme according to the present invention to the mammal sufficient to stimulate production of antibodies specific for *S. pyogenes* DNase B.

Yet another aspect of the present invention is a method for treating cystic fibrosis in a patient with cystic fibrosis. The method comprises:

(1) generating an aerosol of a purified enzymatically active DNase B enzyme according to the present invention; and (2) administering the aerosol to a patient with cystic fibrosis in a quantity sufficient to reduce lung fluid viscosity in the patient.

Figure 9:
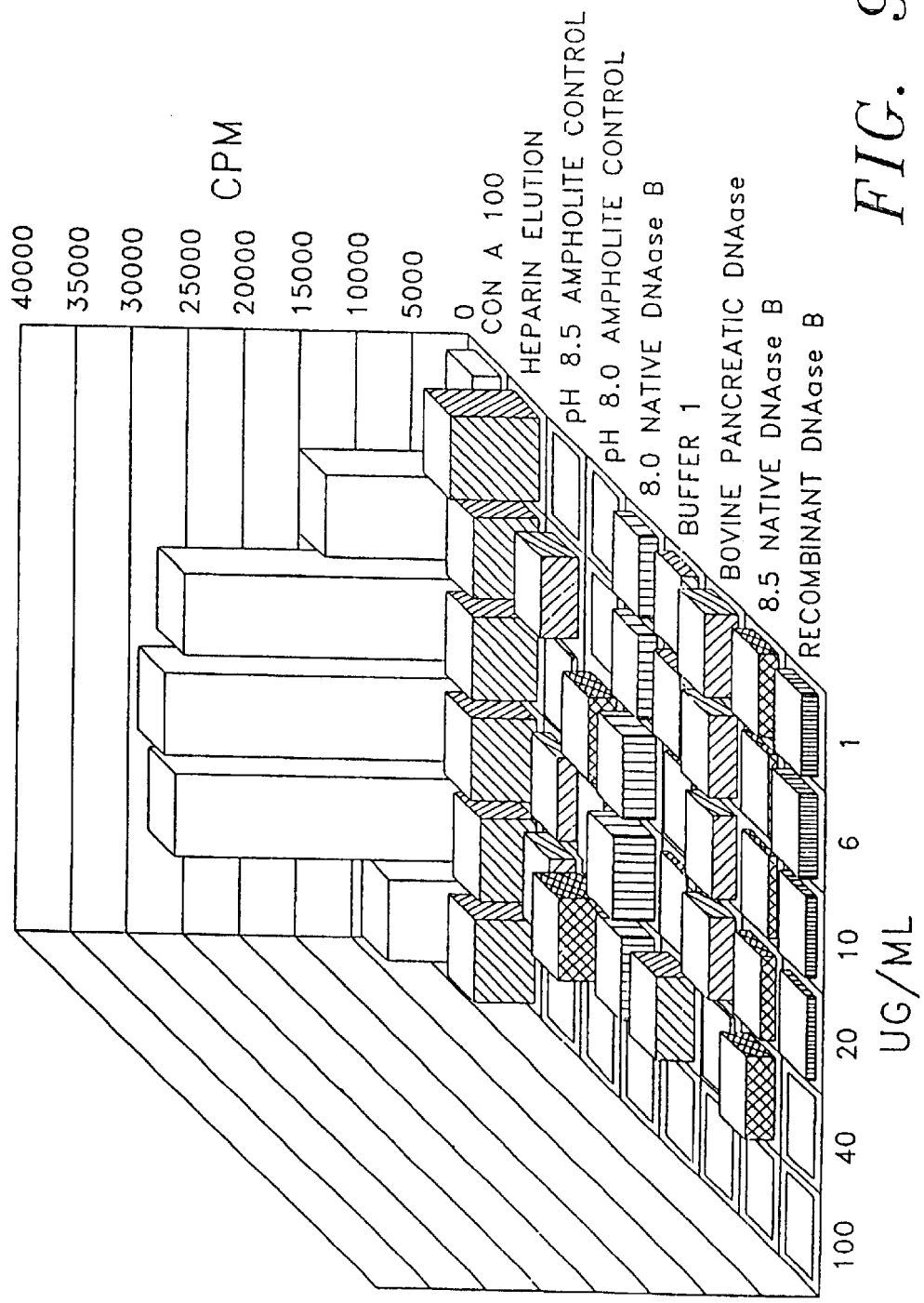

BRIEF DESCRIPTION OF THE DRAWINGS

These and other features, aspects and advantages of the present invention will become better understood with reference to the following description, appended claims, and the accompanying drawings where:

FIG. 1 shows a partial restriction map of the region containing cloned DNase B, indicating the region of chimeric DNA in the clone and the location of the gene for DNase B;

FIG. 2 shows the locations of subclones of the cloned DNA of FIG. 1 and an indication of nuclease activity produced by the subclones;

FIGS. 3A–3C show the DNA sequence of the clone whose partial restriction map is shown in FIG. 1;

FIG. 4 shows the amino acid sequence of the recombinant DNase B protein derived from the DNA sequence of FIG. 3, with the amino terminus determined as the result of sequencing of purified recombinant DNase B;.

FIGS. 5A–5B show the DNA sequence of a construction to fuse the bacteriophage λ promoter to the DNA coding for the DNase B sequence, together with the primers used for PCR in forming the construction;

FIG. 6 is a graph depicting the inactivation of recombinant DNase B by human anti-DNase B serum;

FIG. 7 shows the DNA sequence upstream of the open reading frame in the cloned DNA and the consensus sequence of an *E. coli* promoter;

FIG. 8 is a correlation curve indicating the agreement between determination of anti-DNase B antibody in human serum using recombinant DNase B enzyme and using commercially available DNase B enzyme isolated from *S. pyogenes*; and FIG. 9 is a graph indicating the essential absence of mitogenic activity from both recombinant DNase B and purified preparations of naturally occurring DNase B.

FIGS. 10A–10B show the DNA sequence of a genetic construction that is a component of a vector expressing DNase B in *Escherichia coli* that is processed identically to the native *S. pyogenes* DNase B (SEQ ID NO: 14), as well as the resulting protein sequence (SEQ ID NO: 15).

DESCRIPTION

In order to meet the need for a commercially useable source of *Streptococcus pyogenes* DNase B enzyme, we have cloned the gene for DNase B from *S. pyogenes* genomic DNA into *Escherichia coli*. Despite the considerable evolutionary difference between *S. pyogenes* and *E. coli*, as indicated by the considerable divergence in the sequence of the 18 S ribosomal RNAs of the two species, as well as the substantial difference in morphology and other taxonomic characteristics (*E. coli* is a gram-negative bacillus while *S. pyogenes* is a gram-positive coccus), we have achieved such a high level of expression in *E. coli* of the cloned gene and of activity of the expressed protein that screening could be performed by an enzymatic assay dependent on the activity of the expressed protein.

I. Cloning and Expression of Streptococcus DNase B Gene in *E. coli*

The cloning and expression of the *Streptococcus pyogenes* DNase B gene in *E. coli* requires the following steps, which are optimized carefully to achieve cloning of the intact gene in a form in which active enzyme is expressed from the gene:

(1) isolation of genomic DNA;

(2) preparation of genomic DNA fragments for DNA cloning;

(3) incorporation of DNA fragments into cloning vectors;

(4) infection of bacteria and selection; and (5) expression and screening;

(6) characterization of the clone and DNA sequencing.

A. Isolation of Genomic DNA

Genomic DNA is preferably isolated from *S. pyogenes* under conditions minimizing activity of endogenous nucleases as well as other factors that can degrade or denature DNA. This requires cell lysis and degradation of protein. A preferable method for lysing cells is incubation with the proteolytic enzyme achromopeptidase at 65° C., followed by incubation with the chaotropic detergent sodium dodecyl sulfate (SDS). This procedure is most preferably carried out in the presence of a chelating agent such as EDTA. Alternatively, other proteases such as pronase and proteinase K can be used to lyse the cells. Other lysis procedures are known in the art. (S. Horinouchi et al., "A New Isolation Method of Plasmid Deoxyribonucleic Acid from *Staphylococcus aureus* Using a Lytic Enzyme of *Achromobacter lyticus*," *Agric. Biol. Chem.* 41:2487–2489 (1977)).

Preferably, DNA is then extracted with phenol or phenol-chloroform and the extracted DNA is precipitated with ethanol. A suitable extraction sequence is two extractions with an equal volume of phenol, followed by one extraction with a 1:1 mixture of phenol/chloroform (Example 1). The extraction buffer preferably contains a chelating agent such as EDTA to minimize nuclease activity. Such techniques are well known and are described, for example in D. M. Wallace, "Large- and Small-Scale Phenol Extractions," *Meth. Enzymol.* 152:33–40 (1987) and in D. M. Wallace, "Precipitation of Nucleic Acid," *Meth. Enzymol.* 152:41–48 (1987).

A suitable source of DNA is strain ATCC No. 14289 of *S. pyogenes*, also known as C203S, a non-M containing variant of strain C203. However, similar techniques could be used for other strains of *S. pyogenes* that contain the gene for DNase B.

Preferably, the isolated DNA is treated with RNase A after extraction and ethanol precipitation, then further purified in a cesium chloride gradient.

B. Preparation of DNA Fragments for Cloning

The isolated genomic DNA is preferably fragmented before cloning. Most preferably, fragmentation is performed by passing the DNA through a syringe needle, most preferably a 25-gauge syringe needle, about 300 times. This results in sheared DNA having an average size of approximately 6–8 kb.

In a less preferred alternative, partial digestion with a restriction endonuclease can be used, such as Sau 3A or Mbo I. This is described, for example, in A. -M. Frischauf, "Digestion of DNA: Size Fractionation," *Meth. Enzymol.* 152:183–189 (1987), incorporated herein by this reference.

C. Incorporation of DNA Fragments Into Cloning Vectors

The next step is the incorporation of the DNA fragments into the appropriate cloning vector. Such a cloning vector typically comprises the DNA sequence coding for *S. pyogenes* DNase B operatively linked to at least one control sequence compatible with a suitable bacterial host cell. Such control sequences include operators and promoters. Suitable promoters include bacteriophage λ $p_L$ promoter, a hybrid trp-lac promoter, and bacteriophage T7 promoter. The cloning vector preferably also comprises a suitable ribosome-binding site for expression. A preferred cloning vector is λgt11 (R. A. Young and R. W. Davis, *Proc. Natl. Acad. Sci. USA* 80:1194 (1983), which allows expression controlled by a lac promoter incorporated into the vector and operatively linked to the cloned DNA. Other suitable cloning vectors are well-known in the art and are described, for example, in J. Sambrook et al., "Molecular Cloning: A Laboratory Manual" (2d ed., Cold Spring Harbor Laboratory Press, Cold Spring Harbor, New York, 1989), vol. 3, ch. 17, entitled "Expression of Cloned Genes in *Escherichia coli*", and incorporated herein by this reference. For phage λgt11, the DNA is inserted into an Eco RI site. For such cloning the sheared DNA is preferably repaired using *E. coli* ligase and then T4 DNA polymerase, followed by the addition of Eco RI linkers. These Eco RI-terminated fragments can be ligated to λgt11 arms after digestion with Eco RI restriction endonuclease. Preferably, during this digestion procedure, the internal Eco RI sites are blocked by the use of Eco RI methylase, as the restriction endonuclease does not digest DNA methylated at the adenine residues in the recognition site by the methylase.

After completion of the ligation reaction, the DNA is packaged into bacteriophage λ heads in vitro using a mixture of extracts prepared from bacteria infected with bacteriophage λ mutants in genes required for assembly of phage particles. Packaging procedures are well-known in the art and are described, e.g. in Sambrook et al., supra, vol. 1, pp. 2.95–2.108.

D. Infection of Bacteria and Selection

The phage particles assembled by in vitro packaging are used to infect susceptible *E. coli* bacteria. A particularly preferred strain of bacterial host cells is Y1090 (-pMC9), that is, lacking the pMC9 plasmid. A suitable method is to overlay the plaques with a top agar overlay of DNase test agar (Difco, Detroit, Mich.) containing 0.01% toluidine blue O as a color indicator. This allows detection of plaques expressing the DNase B gene.

The unexpectedly high level of expression of the DNase B gene in this system allowed direct detection of positive clones by direct detection of the resulting enzymatic activity, without a need for immunological screening, which is commonly required for the detection of cloned gene products.

A process for producing substantially purified *Streptococcus pyogenes* DNase B enzyme using transfected host cells can comprise:

(a) culturing a bacterial host cell transformed with a suitable expression vector which can be a bacteriophage λ derivative;

(b) using the cultured transformed bacterial host cell to express the DNase B enzyme; and (c) purifying the enzyme from the cultured transformed bacterial host cell.

E. Characterization of the Clone and DNA Sequencing

Figure 2:
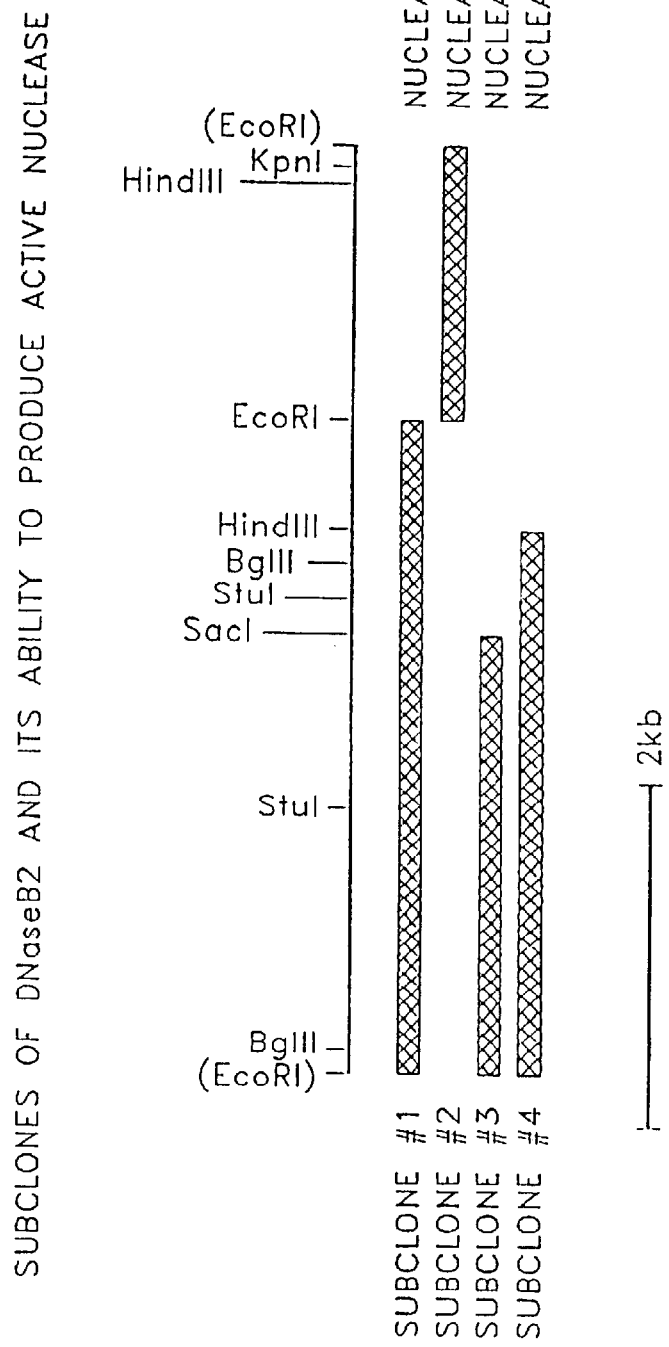

The λgt11 phage containing the *S. pyogenes* DNase B gene (designated 2–6) was isolated and DNA was prepared from the phage. This clone was analyzed by restriction analysis and the results are shown in FIG. 1. Analysis of Eco RI and Eco RI/Sac I subclones for the presence of nuclease activity indicates that part of the DNase B gene was located within the internal Sac I to the Eco RI region, as shown in FIG. 2.

Sequencing of the cloned DNA can be performed using standard techniques, e.g. the Sanger dideoxynucleotide chain termination method. Sequence analysis can be initiated by priming synthesis within the λgt11 phage across the suspected region of DNase activity. Results of such sequencing are shown in FIG. 3.

The cloned DNA whose sequence is shown in FIG. 3 incorporates a lengthy open reading frame (ORF). The amino acid sequence derived from translation of this ORF is shown in FIGS. 3 and 4. The amino acid sequence of the 5'-terminal portion of this ORF starting at amino acid 44 (Gln) is consistent with the amino acid sequence derived by sequencing purified naturally occurring *S. pyogenes* DNase B (Section IV).

Accordingly, the invention encompasses substantially purified DNA comprising DNA encoding an amino acid sequence selected from the group consisting of the amino acid sequence of: (i) *Streptococcus pyogenes* DNase B enzyme as shown in FIG. 4; and (ii) a sequence encoding a functional equivalent of *S. pyogenes* DNase B enzyme. The DNA is substantially free of DNA that does not encode the amino acid sequence of FIG. 4 or a functional equivalent of *S. pyogenes* DNase B enzyme except for a leader peptide fused to the amino terminus of *S. pyogenes* DNase B enzyme. As discussed below, the translation product produced from the open reading frame includes a leader peptide.

In this context, the term "functional equivalent" refers to a protein possessing DNase activity detectable in the generally used assays for *S. pyogenes* DNase B and cross-reacting to at least a detectable extent with antibodies against substantially purified DNase B. The term "functional equivalent" includes, but is not limited to, proteins whose sequence differs from the sequence of FIG. 4 by one or more conservative amino acid substitutions. Such conservative amino acid substitutions include, but are not limited to, substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Also within the scope of the present invention are DNA sequences comprising a portion of the sequence of FIG. 3 of sufficient size and specificity to serve as a reactant in a reaction requiring specific base hybridization. Such a DNA sequence can be a primer for an amplification reaction such as the polymerase chain reaction (PCR), ligase chain reaction (LCR), or other amplification reaction. Alternatively, the DNA sequence can be a hybridization probe. Preferably, the DNA sequence is at least 10 bases long; more preferably, the sequence is at least 50 bases long.

F. Insertion of the Cloned Gene for *S. pyogenes* DNase B into *E. coli* Expression Plasmid Δ33 Producing DNase B Under Regulation of the Bacteriophage λpL Promoter The cloned gene for *S. pyogenes* DNase B can be transferred to the *E. coli* expression plasmid Δ33, which expresses the cloned gene under the control of the bacteriophage λ promoter pL. The *S. pyogenes* DNase B gene is preferably inserted into the expression plasmid by using PCR to attach modified ends to the DNase B gene from the λ2-6 clone. The following nucleotides can be used as primers for the PCR reaction following standard PCR procedures with *Thermus aquaticus* DNA polymerase:

```
        A: 5'-T-A-A-C-G-G-A-T-C-C-G-A-A-T-C-T-A-C-T-T-G-G-A-   (SEQ ID NO:2)
    T-C-A-A-G-A-C-G-G-G-T-T-T-T-T-C-T-3'

B: 3'-T-C-T-T-T-T-T-C-G-T-T-A-C-T-A-A-C-G-G-C-A-G-T-A-   (SEQ ID NO:3)
    A-C-G-G-G-G-C-C-C-A-G-C-T-G-G-G-C-C-5'.
```

These primers can be used with the λgt11 DNase B clone 2-6 DNA as a template for amplification. The resulting amplification products can be digested with the endonuclease Bam HI and Sal I prior to insertion into the Δ33 expression vector. This creates a translational fusion regulated by the pL promoter. A suitable strain of *E. coli* (C600C1$^+$, gal K$^-$) is transformed with the inserted DNA, and bacteria containing the plasma can be selected by selection with ampicillin. DNA can be prepared from these colonies by standard minipreparation techniques, e.g., those described in F. M. Ausubel et al., "Current Protocols in Molecular Biology" (John Wiley & Sons, New York, (1987)

§ 1.6, followed by cutting the isolated plasmid with the appropriate restriction endonucleases (Bam HI and Sal I) to determine if the plasmid comprise the desired recombinant fragment. Plasmids of the desired construction can be introduced into an *E. coli* host strain that is subject to induction by the nalidixic acid protocol, as described in J. E. Mott et al., "Maximizing Gene Expression from Plasmid Vectors Containing the λpL Promoter: Strategies for Overproducing Transcription Termination Factor ρ," *Proc. Natl. Acad. Sci. USA* 82:88–92 (1985), incorporated herein by reference. It is known in the art that nalidixic acid damages DNA and induces recA protein, a recovery protein for *E. coli*. The recA protein has protease activity, which leads to inactivation of λCI$^+$ repressor; this inactivation leads to over-expression by the pL promoter. Other methods of activating transcription from the pL promoter can also be used. When nalidixic acid induction is used, substantial quantities of DNase B are secreted outside the cell.

II. Properties of Recombinantly Produced Enzyme

The recombinantly produced enzyme from λ 2-6 phage contains a leader peptide fused to the amino terminus of the DNase. This leader peptide has the sequence M-N-L-L-G-S-R-R-V-F-S-K-K-C-R-L-V-K-F-S-M-V-A-L-V-S-A-T-M-A-V-T-T-V-T-L-E-N-T-A-L-A-R (SEQ ID NO: 1).

Immunoinhibition assays (Example 7) demonstrate that recombinant *S. pyogenes* DNase B is inhibited by anti-DNase enzyme in human serum in a manner identical to non-recombinant DNase B enzyme, based on the ability of the DNase to use a DNA-dye complex as substrate.

III. Mutants of Recombinantly Produced DNase B Enzyme

Another aspect of the invention is mutants or variants of the *S. pyogenes* DNase B gene which have altered DNase B activity. These mutant DNase B enzymes may have higher or lower levels of nuclease activity. These mutants include mutants of the protein whose amino acid sequence is shown in FIG. 4 in which at least one of the following mutations occurs:

(a) a deletion of one or more amino acids from the sequence of FIG. 4;

(b) an insertion of one or more naturally-occurring L-amino acids into the sequence of FIG. 4; and (c) replacement of at least one of the amino acids of FIG. 4 with an alternative naturally occurring L-amino acid.

Such mutant DNase B proteins encoded by mutant DNase B genes can be used for their nuclease activity or for their immunogenicity. Preferably, when used for their immunogenicity, these mutants contain single amino acid changes which remove all nuclease activity, but maintain all significant immune epitopes, so that they substantially retain the antigenic reactivity of natural *S. pyogenes* DNase B enzyme. Thus, high level expression in *E. coli* can be achieved without altering human antibody reactivity with the altered DNase B. Such mutants or variants can be prepared according to techniques well-known in the art, such as those described in Sambrook et al., supra, Ch. 15, entitled "Site-Directed Mutagenesis of Cloned DNA." Such technique include linker-insertion mutagenesis, linker-scanning mutagenesis, oligonucleotide-mediated mutagenesis with the polymerase chain reaction (PCR) technique, and growth in highly mutagenic strains.

When used for their nuclease activity, the mutant proteins will typically be functional equivalents of the recombinant DNase enzyme of FIG. 4, as that term is defined above, but are not necessarily limited thereto.

IV. Use of Leader Peptide for *S. pyogenes* DNase b Enzyme

The leader peptide for DNase B, with an amino acid sequence of M-N-L-L-G-S-R-R-V-F-S-K-K-C-R-L-V-K-F-S-M-V-A-L-V-S-A-T-M-A-V-T-T-V-T-L-E-N-T-A-L-A-R (SEQ ID NO: 1), can be used for expression and production of recombinant proteins in bacteria. A suitable process for the use of the leader peptide comprises:

(1) fusing the DNA coding for the protein to DNA coding for a leader peptide with an amino acid sequence of M-N-L-L-G-S-R-R-V-F-S-K-K-C-R-L-V-K-F-S-M-V-A-L-V-S-A-T-M-A-V-T-T-V-T-L-E-N-T-A-L-A-R (SEQ ID NO: 1) so that the fused DNA forms a recombinant protein with a single reading frame with the leader peptide being at the amino-terminus of the protein;

(2) introducing the fused DNA into the prokaryote; and (3) expressing the fused DNA in the prokaryote so that the recombinant protein is produced in a recoverable quantity.

The bacterium can be *Escherichia coli* or, alternatively, a gram-positive bacterium such as Staphylococcus, Streptococcus, and Streptomyces.

Preferably, the recombinant protein is excreted by the prokaryote into its culture medium so that it can be recovered from the culture medium.

Methods for fusing the DNA segment coding for leader peptide to the gene for the protein to be produced are well-known in the art and include blunt-end ligation. Blunt-end ligation is typically performed with T4 ligase (V. Sgaramella & H. G. Khorana, "Studies on Polynucleotides. CXII. Total Synthesis of the Structural Gene for an Alanine Transfer RNA from Yeast. Enzymic Joining of the Chemically Synthesized Polydeoxynucleotides to Form the DNA Duplex Representing Nucleotide Sequence 1 to 20," *J. Mol. Biol.* 72:427 (1972); V. Sgaramella & S. D. Ehrlich, "Use of the T4 Polynucleotide Ligase in the Joining of Flush-Ended DNA Segments Generated by Restriction Endonucleases," *Eur. J. Biochem.* 86:531 (1978)), and is preferably performed in the presence of condensing agents such as polyethylene glycol or hexamminecobalt chloride.

Alternatively, if a suitable restriction endonuclease exists that generates cohesive ends and can cut both the portion of the DNA coding for the linker that corresponds to the carboxyl-terminus of the linker and the portion of the gene coding for the protein that corresponds to the amino-terminus of the protein, the restriction endonuclease can be used to generate cohesive ends for ligation.

V. Purification of *S. pyogenes* DNase B Enzyme

A. Purification of Natural *S. pyogenes* DNase B

Another aspect of the present invention is an improved procedure for purification of natural *S. pyogenes* DNase B enzyme. This procedure was developed by using polyacrylamide gel analysis of the DNase B found in the commercial assay reagent and a comparison to the behavior on gel electrophoresis of the natural enzyme. The purification procedure employs the following steps, starting with a crude extract or other source of the enzyme: (1) absorption to and elution from diethylaminoethyl cellulose to produce a first eluate; (2) chromatography of the first eluate on phenyl agarose to produce a second eluate; (3) chromatography of the second eluate on heparin agarose to produce a third eluate; and (4) chromatofocusing of the third eluate to produce substantially purified DNase B enzyme. The chromatofocusing is preferably carried out on a mono-P column.

Preferably, the purified DNase is further fractionated to remove ampholytes used during chromatofocusing using reverse-phase high-pressure liquid chromatography on C4 with a gradient of 0.1% trifluoroacetic acid in water and 0.08% trifluoroacetic acid in acetonitrile.

The purification procedure results in substantially purified *Streptococcus pyogenes* DNase B enzyme substantially free of proteins other than Streptococcus DNase B enzyme and Streptococcus DNase B enzyme fused at its amino terminus with a leader peptide. The substantially purified protein is substantially free of mitogenic activity (See Example 6 below).

Purification results in two substantially purified DNase B fractions, differing in charge. Each of the fractions is substantially free of the other fraction and other proteins. These fractions are designated as Fraction I, which elutes from the chromatofocusing column at pH 8.55–8.4, and Fraction II, which elutes from the chromatofocusing column at pH 8.22–8.13. Molecular weight data obtained from mass spectroscopy (Example 3), indicates that the difference in molecular weights between Fractions I and II of the purified natural DNase B is consistent with a minor modification of an otherwise identical amino acid sequence. A possible modification is deamination, which would cause the appropriate pI shift.

The purified protein can be sequenced. The first 23 amino acids of both fraction I and II produced the following readable sequence: Q-T-Q-V-S-N-D-V-V-L-N-D-G-A-S-X-Y-L-N-E-A-L-A (SEQ ID NO: 4), where X represents tryptophan or lysine.

As detailed below, this sequence represents a means for designing probes suitable for hybridizing with at least a DNA sequence coding for the amino-terminal amino acid sequence of the gene.

B. Purification of Recombinantly Produced *S. pyogenes* DNase B Enzyme

Recombinant *S. pyogenes* DNase B, which is present at a high level in the chimeric cells, can be purified by similar techniques. For example, the recombinant DNase B can be purified from phage lysate collected from *E. coli* infected with λDNase B 2-6 phage by chromatography on Q-sepharose (trimethylaminomethyl agarose), ammonium sulfate precipitation, chromatography on heparin sepharose, and chromatography on Q-sepharose. The recombinant DNase B produced in *E. coli* transfected with recombinant plasmid Δ33 expressing *S. pyogenes* DNase B from the pL promoter can be purified by chromatography on heparin sepharose, chromatography on Q-sepharose, and reverse phase high pressure liquid chromatography. Other purification methods are known and can be used by one skilled in the art.

VI. Preparation of DNA Probes Capable of Hybridizing to Cloned DNA

Another aspect of the invention is preparation of a single-stranded nucleic acid probe hybridizing with the DNA sequence coding for the amino-terminal 23 amino acids of the *S. pyogenes* DNase B enzyme with no greater than about a 30% mismatch. The nucleic acid probe can be RNA or DNA. Preferably, when the probe is DNA, the degree of mismatching is no greater than about 10% under standard stringent conditions, i.e., those described in F. Ausubel et al., in *Current Protocols in Molecular Biology* (Wiley-Interscience, New York, 1990).

Suitable sequences of such probes can be derived by using the codon usage table for enteric bacterial genes given for the relevant amino acids in Table 1.

TABLE 1

CODON USAGE FOR AMINO ACIDS IN AMINO-TERMINAL REGION OF *S. PYOGENES* DNASE

| Codon | Frequency | Codon | Frequency |
|---|---|---|---|
| Gln (O) | | Thr (T) | |
| CAG | 0.86 | ACC | 0.55 |
| CAA | 0.14 | ACU | 0.35 |
| | | ACG | 0.07 |
| | | ACA | 0.04 |
| Val (V) | | Ser (S) | |
| GUU | 0.51 | UCC | 0.37 |
| GUA | 0.26 | UCU | 0.34 |
| GUG | 0.16 | AGC | 0.20 |
| GUC | 0.07 | UCG | 0.04 |
| | | AGU | 0.03 |
| | | UCA | 0.02 |
| Asn (N) | | Asp (D) | |
| ACC | 0.94 | GAC | 0.67 |
| AAU | 0.06 | GAU | 0.33 |
| Leu (L) | | Gly (G) | |
| CUG | 0.83 | GGU | 0.59 |
| CUC | 0.07 | GGC | 0.38 |
| CUU | 0.04 | GGG | 0.02 |
| UUG | 0.03 | GGA | 0.00 |
| UUA | 0.02 | | |
| CUA | 0.00 | | |
| Ala (A) | | Trp (W) | |
| GCU | 0.35 | UGG | 1.00 |
| GCA | 0.28 | | |
| GCG | 0.26 | | |
| GCC | 0.10 | | |
| Tyr (Y) | | Glu (E) | |
| UAC | 0.75 | GAA | 0.78 |
| UAU | 0.25 | GAG | 0.22 |

One example of such a probe is shown below:

Probe 1: C-A-P-U-A-C-N-C-A-R-T-N-W-S-N-A-A-Y-G-A-Y-G-T (SEQ ID NO:5).

In this sequence, R represents a purine (i.e., A or G) Y represents a pyrimidine (T or C), S represents G or C, W represents A or T, and N represents any of the four common deoxyribonucleotides (i.e., A, G, C, or T).

This probe, and other probes, can be synthesized by procedures well-known in the art, such as solid-phase DNA synthesis by the phosphotriester or phosphite triester methods, as disclosed, e.g., in "Nucleic Acids in Chemistry and Biology" (G. M. Blackburn & M. J. Gait, eds., IRL Press, Oxford, 1990), ch. 3. pp. 106–123.

VII. Use of Upstream Promoter Associated with *S. pyogenes* DNase B

Another aspect of the present invention is the isolation and use of an upstream promoter originally associated with the *S. pyogenes* DNase B gene to express a protein other than DNase B. The detection of this promoter sequence is described below in Example 11.

The promoter sequence is retained in the λ2-6 clone. This sequence includes a start site for transcription and sites substantially homologous to the consensus −10 and −35 sites for bacterial promoters (Example 11). This substantially purified promoter sequence is within the scope of the invention.

A method of using this promoter sequence for expressing a protein other than DNase B comprises:

(1) separating the promoter originally associated with the S. pyogenes DNase B gene from the S. pyogenes DNase B gene;

(2) operatively linking the promoter with a structural gene for a S. pyogenes protein other than the gene for DNase B; and (3) expressing the protein encoded by the structural gene.

The protein can be expressed in S. pyogenes or in a prokaryote other than S. pyogenes, such as E. coli. The promoter can be incorporated in a vector or a plasmid for expression of a gene operatively linked to the promoter in the vector or plasmid.

VIII. Use of Substantially Purified DNase B Enzyme

The present invention also encompasses several uses of the substantially purified S. pyogenes DNase B enzyme, whether purified from natural sources or produced by recombinant DNA techniques.

A. Use of Enzyme for Preparation of Antibodies

Among the uses of the enzyme prepared by methods according to the present invention is the preparation of antibodies. The antibodies can either be polyclonal or monoclonal. Preparation of both polyclonal and monoclonal antibodies is described in E. Harlow and D. Lane, "Antibodies: A Laboratory Manual" (Cold Spring Harbor Laboratory, Cold Spring Harbor, N.Y., 1988). pp. 53–318. The resulting antibodies can be used for detection of the S. pyogenes enzyme, i.e., in suspected cultures.

B. Use of Enzyme for Detection of Anti-DNase B Antibody

An important use for the substantially purified S. pyogenes DNase B enzyme of the present invention is the detection of anti-S. pyogenes DNase B antibodies, such as in serum. As described above, the presence of such antibodies is indicative of active S. pyogenes infection and a warning signal that serious suppurative sequelae may occur.

One method of detecting the anti-DNase B antibody employs the fact that the antibody is capable of inhibiting the activity of the enzyme. Such a method can comprise the following steps:

(1) providing a test sample suspected of containing anti-S. pyogenes DNase B antibody;

(2) adding a quantity of the S. pyogenes DNase B enzyme according to the present invention to the test sample, the quantity being sufficient to produce a detectable level of enzymatic activity in the absence of inhibition of the enzymatic activity by anti-DNase B antibody in the test sample; and (3) determining the level of activity of DNase B enzyme in the test sample by performing an enzyme assay to detect and/or determine the anti-S. pyogenes antibody in the test sample.

The enzyme assay can be performed by standard methods, such as the DNA-dye complex degradation assay of Wampole Laboratories (Cranbury, N.J.). This assay is based on the ability on the DNase to use a DNA-dye complex as substrate. This complex exhibits a maximum absorption wavelength of 642 nm. However, as the DNA-dye complex is degraded by the DNAse, there is a shift in the maximum absorption wavelength and a decrease in the absorption at 642 nanometers. Other enzymatic assays are available, such as viscosimetric assays, which measure the ability of the enzyme to depolymerize long DNA molecules, thus greatly reducing the viscosity of solutions containing DNA. Alternatively, assays can be performed by using radioactive DNA as a substrate and quantitating the release of radioactivity after incubation. Other methods for the assay of deoxyribonuclease are well known in the art.

An alternative assay for anti-DNase B enzyme antibody in serum is an ELISA assay. This assay comprises:

(1) binding the S. pyogenes DNase B enzyme of the present invention to a solid support;

(2) reacting a test sample suspected of containing anti-S. pyogenes DNase B antibody with the S. pyogenes DNase B enzyme to bind the antibody to the enzyme and thus to the solid support; and (3) detecting the antibody bound to the solid support to detect and/or determine the antibody in the test sample.

ELISA procedures are well known in the art and are described, e.g. in P. Tijssen, "Practice and Theory of Enzyme Immunoassays" (Elsevier, Amsterdam, 1985). The solid support used is typically plastic, such as polystyrene, but other solid supports, such as nitrocellulose, can also be used. The detection of the bound antibody is typically performed by adding a second antibody specific for the first antibody; the second antibody does not bind the S. pyogenes DNase B enzyme. Such an antibody can be, for example, enzyme-labeled anti-human immunoglobulin G. The enzyme label is typically alkaline phosphatase, λ-galactosidase, glucose oxidase, or horseradish peroxidase. Such enzymes give products that have optical absorption in the visible spectrum, and can be detected either visually or with a spectrophotometer.

Other techniques of detecting and/or determining the formation of antigen-antibody complexes can also be used to assay anti-DNase B antibody in serum. These techniques detect an aggregated antigen-antibody complex, here an enzyme-antibody complex, by a change in light absorption or scattering. In general, such an assay comprises:

(1) preparing a buffered solution of the DNase B of the present invention;

(2) reacting the buffered DNase B solution with a test sample suspected of containing anti-S. pyogenes DNase B antibody; and (3) detecting a reaction between the DNase B and the anti-DNase B antibody by observing and/or measuring a change in light absorption and/or light scattering in the solution.

The DNase B can be attached to higher molecular weight carriers, such as latex polymers, plastic or gel beads, and the like.

In a number of applications, it is particularly advantageous to attach the enzyme to latex particles. This can provide several advantages, including stabilization of the enzyme and increased sensitivity of detection, either by turbidimetry or nephelometry. The latex agglutination assay format is popular for clinical immunoassays.

Many different coating methods can be used in attaching DNase B to latex particles. Some of the widely used methods are: (1) attachment by adsorption to latex particles; (2) attachment by covalent coupling via carboxyl groups on the latex particles; and (3) attachment by covalent coupling via aldehyde groups on the latex particles.

The size of the latex particles used for attachment can range from about 15 nm to about 1000 nm in diameter, depending on the application.

The reaction between the DNAse B and the anti-DNase B can be detected by nephelometry or turbidimetry. Another alternative method for detecting anti-DNase B antibody is capillary electrophoresis.

C. Other Uses

The recombinant protein can be used for vaccine development to immunize against *S. pyogenes* in susceptible individuals, and also can be used as an aerosol in the treatment of lung viscosity symptoms in diseases such as cystic fibrosis when the viscosity is due to exudates containing high concentrations of DNA.

For use as a vaccine, a quantity of a purified *S. pyogenes* DNase B enzyme according to the present invention is administered to a mammal. The quantity is sufficient to stimulate production of antibodies specific for *S. pyogenes* DNase B.

Administration is typically by injection, and can be intravenous, intramuscular, subcutaneous, intradermal, or by other routes. The DNase B enzyme can be administered with an adjuvant to increase the immune response. Suitable adjuvants are well known in the art and include complete and incomplete Freund's adjuvant, as well as aluminum hydroxide with or without heat-killed *Bordetella pertussis* bacteria. The enzyme can be aggregated, precipitated, or coupled to insoluble matrices.

One particularly suitable enzyme according to the present invention for use in immunization is a mutant enzyme in which the DNase activity is completely or substantially eliminated and the antigenicity is wholly or substantially retained.

A method of use of enzymatically active DNase B enzyme according to the present invention can comprise:

(1) generating an aerosol of purified enzymatically active DNase B enzyme according to the present invention; and (2) administering the aerosol to a patient with cystic fibrosis in a quantity sufficient to reduce lung fluid viscosity in the patient.

Administration of the aerosol can be performed using inhaler devices well-known in the art and frequently used to deliver steroids and other drugs to the respiratory tract by inhalation.

EXAMPLES

The following examples are intended for illustrative purposes only and are not intended to limit the invention.

Example 1

Cloning of *Streptococcus Pyogenes* DNase B Gene

The *S. pyogenes* DNase B gene was identified by an activity based colorimetric detection of nuclease activity produced from a recombinant λ bacteriophage. The phage was a product of a λ library containing sheared DNA purified from *S. pyogenes* (Lancefield Group ATCC No. 14289) genomic DNA.

Preparation of Chromosomal DNA from *S. pyogenes*

*S. pyogenes* strain ATCC 14289 was streaked onto Todd Hewitt agar plates and incubated at 37° C. for two days. A single colony was used to inoculate one liter of Todd Hewitt broth with 10% calf serum. The culture was allowed to grow to high density at 37° C. with shaking for about 36 hours.

The cells were collected by centrifugation in a Beckman J6 centrifuge at 3500 rpm at 4° C. for 45 minutes. The cell pellet was resuspended in 25 ml of 40 mM Tris, pH 7.5, 1 mM EDTA. The proteolytic enzyme achromopeptidase (60 mg) (Wampole), in 1 ml buffer, was added and the mixture was incubated at 65° C. for one hour. No lysis was visible. A total of 20 ml of 10% SDS was then added, and incubation was continued for one hour. Lysis was very apparent. Fifty milliliters of buffer was then added to reduce the concentration of SDS to 2.5%.

The mixture was extracted twice with an equal volume of phenol, followed by one extraction with phenol/chloroform (1:1). The DNA in the aqueous phase was precipitated by ethanol. The DNA was recovered by centrifugation. The pellet was resuspended in 4 ml of 10 mM Tris-HCl, pH 7.5, 1 mM EDTA (TE). RNase A (50 μl at 10 mg/ml) was added and the mixture was incubated at 37° C. for three hours.

The DNA was further purified in a cesium chloride gradient. The final concentration of DNA was about 0.5 mg/ml.

Construction of *S. pyogenes* Library in λgt11

The isolated chromosomal DNA (300 μml) was added to 200 μl of TE buffer. The mixture was passed through a 1 ml syringe with a 25-gauge needle about 300 times to shear the DNA to an average size of 6 kb.

The sheared DNA (150 μl) was treated with *E. coli* ligase to repair existing nicks in the DNA which might otherwise have become gaps with subsequent manipulations. To 150 μl of DNA was added 20 μl of 10× *E. coli* ligase buffer (0.5 M Tris-HCl, pH 7.6, 100 mM $MgCl_2$, 100 mM dithiothreitol, and 500 μg/ml bovine serum albumin), 20 μl of $NAD^+$ (36 mM) and 7 μl of *E. coli* ligase (New England Biolabs, Beverly, Mass., 4 units/μl) was added to the DNA and the mixture was left at room temperature for four to five hours. The ligase was heat killed at 65° C. for 15 minutes. The DNA was precipitated by ethanol.

Eco RI sites in the ligase-treated DNA were methylated with Eco methylase following the protocol of the manufacturer (Promega, Madison, Wis.). This was done to block internal Eco RI sites whose cleavage would interfere with the cloning procedure.

The sheared ends of the DNA were repaired with T4 DNA polymerase by adding 30 μl of 0.1 M $MgCl_2$, 20 μl of 2.5 mM of each of the four deoxyribonucleoside triphosphates, and 2 μl of T4 DNA polymerase (3000 U/ml) to the DNA mix after methylation. The reaction was carried out for 15 minutes at room temperature. The mixture was extracted once with phenol/chloroform and then with ether. The DNA in the aqueous fraction was then precipitated with ethanol.

Eco RI linkers were ligated onto the DNA. The linkers used were octamers from New England Biolabs. After linker ligation, the DNA was digested with an excess of Eco RI restriction endonuclease enzyme. DNA of the desired size range, namely 6–8 kb, was purified from an agarose gel after electrophoresis. The DNA was concentrated by ethanol precipitation and was then ready for ligation into λ gt11.

Approximately 2 μg of sheared DNA was ligated with 1 μg of λgt11 arms previously digested with Eco RI restriction endonuclease and in which the terminal phosphate residue had been removed by treatment with alkaline phosphatase. The ligation was carried out with bacteriophage T4 ligase in a total volume of 5 μl. The ligation reaction was performed at 4° C. overnight.

The entire ligation mix was packaged in vitro using the Promega (Madison, Wis.) packaging extract. One μl of packaged phage was plated on a lawn of Y 1090 *E. coli* in the presence of isopropylthio-β-D galactoside (IPTG) and the chromogenic substrate 5-bromo-4-chloro-3-indolyl-β-D-galactoside) (Xgal) approximately 5%. of the plaques were blue. The packaging efficiency was approximately $10^6$ plagues per µg of DNA.

Screening for λ Recombinant Clones with Nuclease Activity

The non-amplified library (10 µl) was plated with 0.1 ml of an overnight culture of LE 392. After five hours, the plates were overlaid with 0.5× BBL DNase test agar plus 0.01% toluidine blue plus 10 mM $MgCl_2$. A total of 10 plates was screened. Forty-four pink plaques (potentially nuclease positive) were rescreened. Nine of the 44 pink plaques consistently rescreened as positive for nuclease activity.

Because the production of S. pyogenes DNase is deleterious to the host E. coli bacteria, the plaque size of these nuclease positive clones was much smaller than for nuclease negative clones. Accordingly, there was selection pressure for accumulating mutations that would lower the nuclease activity, which complicates the task of isolating a stable nuclease positive clone.

One of the advances of the selection and screening procedure of the present invention is to lower the selection pressure allowing stable nuclease positive clones. To do this, E. coli strain Y1090 without the plasmid pMC9 was used as the host for nuclease carrying phage. Plate lysates were used to generate stocks to plaque purify the clones. For this procedure, l the host and phage were plated directly on 0.5× BBL DNase test agar plus 0.01% toluidine blue plus 10 MM $MgCl_2$ directly instead of overlaying after five hours of incubation.

Lysates of the nine recombinant clones were analyzed on SDS-polyacrylamide gels containing DNA. The nuclease in all nine clones retained their activity after SDS denaturation and all have the same apparent molecular weight, approximately 25 kd.

These nine lysates were analyzed on the PhastGel system with IEF 3-9 gels for electrofocusing. After electrophoresis, the gels were overlaid with 3.5 ml DNase substrate (Streptonase B kit) (Difco, Detroit, Mich.) in 1% agarose in TAE (40 mM Tris, 5 mM sodium acetate, 1 mM EDTA, pH 8). The activity bands for all 9 lysates at the edge of the basic end of the gel, suggesting a very high pI for the cloned nuclease. This also suggested that all nine clones contained the same gene.

In particular, one phage showing DNase activity, designated as 2-6 was analyzed further. The λ DNase 2-6 clone was analyzed with restriction endonuclease analysis to characterize the DNA fragment. The S. pyogenes genomic insert in the λ vector in the 2-6 clone was approximately 5.2 kb. The location of the nuclease gene was determined by subcloning smaller regions of the DNase 2-6 clone back into λ gt11 and testing the subclones for nuclease activity. FIG. 2 shows the location of the various subclones and their nuclease activity. Subclones 1 and 4 produced nuclease activity but were very unstable. Subclones 2 and 3 lacked nuclease activity but were stable. The results of this subcloning indicated that at least part of the DNase B gene resides in the internal Sac I/Eco RI fragment. The amino-terminal sequence from the DNase B protein was used in conjunction with the genetic code to generate a set of degenerate oligonucleotides that was used to hybridize to the DNase 2-6 insert and some of the subclones. These oligonucleotides hybridized to the 3.5 kb Eco RI fragment in DNase B 2-6 and the Sac I/Eco RI fragment in subclone 3.

This data, together with the subcloning data, suggest that the transcription of the nuclease gene is very likely from left to right as diagrammed, and the Sac I site is within the DNase B gene.

Mapping of the S. pyogenes DNA adjacent to the 5.2 kb insert was done by genomic DNA blot hybridization. The 3.5 kb and 1.5 kb Eco RI fragments of the λ DNase 2-6 DNA were gel purified and labeled with $^{32}P$ by random priming. The same genomic blots were hybridized with the two probes consecutively. A partial restriction endonuclease map of the insert and its neighboring region in the S. pyogenes chromosome is shown in FIG. 1.

Example 2

Sequencing of the Clone 2-6 Containing S. pyogenes DNase B

Nucleotide sequence analysis was performed on clone 2-6 by the dideoxynucleotide chain termination method of Sanger et al., supra. Sequence analysis was initiated by priming synthesis from within the λgt11 phage of clone 2-6 across the suspected region of DNase activity. The results of sequencing are shown in FIG. 3. The S. pyogenes DNase B is within the first full open reading frame of the sequence.

Example 3

Purification of Native S. pyogenes DNase B

Native S. pyogenes DNase B was purified using a commercial DNase B assay reagent as a marker of the correct nuclease. In other words, polyacrylamide gel electrophoresis results obtained with the DNase B in the commercial kit was compared to the results from gel electrophoresis in extracts produced from S. pyogenes ATCC No. 14289. The purification procedure included: batch absorption on DE-23 diethylaminoethyl cellulose (Whatman) (2) chromatography on phenyl Sepharose® (Pharmacia, Uppsala, Sweden); (3) chromatography on heparin Sepharose® (Pharmacia); and (4) mono-P chromatofocusing (Pharmacia).

Bacterial Cultures

Streptococcus pyogenes ATCC NO. 14289 (American Type Culture Collection, Rockville, Md.), derived from A. Bernheimer C203S (non-M containing variant of C203) was used as the bacterial source for the collection of DNase B-containing culture media, the enzyme being secreted into the culture media by the bacteria. Volumes of brain heart infusion media (1 liter) (Difco Laboratories, Detroit, Mich.) supplemented with 0.01% washed goat red blood cells were inoculated with 1 ml of a fresh overnight culture. These cultures were grown for 20 hours with moderate agitation (300 rpm) at 37° C. in 2 liter Erlenmeyer flasks. Prior to purification the culture medium was clarified and sterilized by filtration using a Pellicon filter (0.22 µm Durapore GVLP membrane) followed by filtration through an 0.45 µm disposable filtration apparatus (Nalgene, Nalge Co., Rochester, N.Y.). Approximately 105 liters of culture media was processed with this procedure.

Batch Absorption to Diethylaminoethyl Cellulose

The clarified media was concentrated by ultrafiltration using the Pellicon apparatus and a 10 K membrane (PLGC, regenerated cellulose) with a filter area of about 0.46 $m^2$ at a flow rate of 120 ml/min, and a pressure of 20 lbs per square inch (1.4 $Kg/cm^2$). The initial volume of 105 liters of media was eventually concentrated to 4 liters with a protein concentration of 2.3 mg/ml.

Diethylaminoethyl cellulose (DEAE-cellulose) (DE23, Whatman, England) was regenerated by washing with 15 volumes of 0.5 M HCl followed by a second wash with 15 volumes of 0.5 M NaOH. After a repetition of the washing with sodium hydroxide, the DEAE-cellulose was washed with water until neutral. Finally, the cellulose was equilibrated overnight in TMC buffer (1 mM Tris, 1 mM MgCl, 1 mM $CaCl_2$, pH 7.5).

The equilibrated wet cellulose (100 g) was added to 500 ml of concentrated S. pyogenes media supernatant. The mixture was shaken at 300 rpm for 20 minutes at 4° C. prior to centrifugation at 3500 rpm for 45 minutes. The cellulose was washed with 450 ml of TMC buffer and the two supernatants were combined.

Chromatography on Phenyl Sepharose

The supernatants from diethylaminoethyl cellulose batch absorption were clarified by filtration through a 0.45 μm membrane. Ammonium sulfate was added to 0.8 M prior to passage through phenyl Sepharose CL 45 (Pharmacia, Uppsala, Sweden) equilibrated with 0.8 M ammonium sulfate, 20 mM sodium phosphate (pH 8.0).

The 80-ml phenyl sepharose column was loaded at 1.85 ml/min with 1100 ml of sample at a concentration of 258 μg/ml. The DNase activity was collected in the flow-through prior to concentration by ultrafiltration using a 10-kd membrane (Diaflo YM10, Amicon Division, W.R. Grace & Co.) The final protein concentration was 0.245 mg/ml, in 55 ml.

Chromatography on Heparin Sepharose

The concentrated effluent from the phenyl-sepharose column was dialyzed against Heparin Buffer A (20 mM HEPES, pH 7.9, 2 mM dithiothreitol, 10 mM $MgCl_2$, 0.2 mM EDTA, 0.1 NaCl, 10% glycerol). A heparin Sepharose CL-6B (Pharmacia) column (80 ml) was equilibrated with the Heparin Buffer A prior to loading at a flow rate of 1.0 ml/min. After washing the column with three volumes of heparin buffer A, a gradient between 0% and 100% buffer B was run at a flow rate of 2.2 ml/min. Buffer B was the same as buffer A except that the concentration of sodium chloride was 1.0 mole/l. The DNase activity eluted at 350 mM NaCl in volume of approximately 250 ml. The DNase activity was concentrated by ultrafiltration.

Mono-P Chromatofocusing

The concentrated DNase fraction was dialyzed against 25 mM diethanolamine, pH 9.5 prior to chromatofocusing. The mono P 5/20 column (Pharmacia, Piscataway, N.J.) equilibrated in the loading buffer (25 nM ethanolamine, pH 9.5), was injected with 500 μl of sample and washed with 9 ml of loading buffer. The column was eluted with 100% buffer B (10% polybuffer 96 (Pharmacia), pH 6.0). The total volume eluted was 34 ml; fractions of 0.5 ml were collected. Two peaks of activity were collected at pH 8.55–8.4 (fractions 25–29), designated herein as Fraction I, and 8.22–8.13 (fractions 34–35), designated herein as Fraction II. The collected fractions were analyzed by isoelectric focusing activity gels, silver staining, and by SDS-polyacrylamide gel electrophoresis.

Reverse Phase High-pressure Liquid Chromatography

Peak fractions from the chromatofocusing column were further purified to remove the ampholytes used for chromatofocusing by reverse phase high pressure liquid chromatography using a C4 column (Beckman System Gold Instrument, Beckman Instruments, Fullerton, Calif.). Samples were loaded in buffer A (0.1% trifluoroacetic acid in water) and a gradient of 0%–100% buffer B (0.8% trifluoroacetic acid in acetonitrile) was used to elute the column at a flow rate of 1 ml/min. Those proteins eluted in 65% buffer B in a volume of about 1 ml.

SDS and Isoelectric Analysis

SDS-polyacrylamide gel analysis of all samples was performed using the PHAST System (Pharmacia LKB, Piscataway, N.J.) automated instrument. SDS-polyacrylamide gel electrophoresis was performed on the PhastGel 10–15% gels. Isoelectric gels were run using the PhastGel IEF 3–9 gels. Silver staining of both the SDS and the isoelectric gels was performed using the PhastSystem automated staining device (Pharmacia LKB). Activity assays of the DNase samples on the isoelectric focusing gels were performed by overlaying the gels after electrophoresis with 5 ml of a 1% melted agarose solution containing phosphate buffered salts and 1 ml of reconstituted DNase substrate dye (Wampole). Incubation of the IEF gels with the substrate overlay at room temperature resulted in the detection of activity by the conversion of the blue substrate dye to a pink color centered around the nuclease activity. Activity assays of SDS-denatured samples were performed using an SDS-14% polyacrylamide gel that was polymerized in the presence of 500 μg/ml herring testes DNA. After electrophoresis, the gels were rinsed with water and equilibrated with 40 mM Tris-HCl, pH 7.5, 2 mM $MgCl_2$, 0.02% sodium azide for 2 hours at 37° C. Ethidium bromide was added to 1 μg/ml in order to observe the nuclease activity visible as a result of the degradation of the DNA by the nuclease.

Protein Sequencing

The amino-terminal sequences of Fractions I and II of the purified DNase were determined using an Applied Biosystems (Foster City, Calif.) 477 sequenator. Samples of each of the purified enzymes (Fractions I and II) were loaded on to an Applied Biosystems (Foster City, Calif.) 470 Protein Sequencer. The first 23 amino acids of both Fraction I and II produced the following readable sequence: Q-T-Q-V-S-N-D-V-V-L-N-D-G-A-S-X-Y-L-N-E-A-L-A (SEQ ID NO: 4), where X stands for an amino acid that cannot be definitely identified, but is most likely either tryptophan or lysine.

Mass Spectroscopy Analysis

Ion-spray mass spectral analysis was performed on recombinant DNase B (Example 1) and on Fractions I and II of the purified native DNase B using the Finnigan MAT TSQ 700 triple-stage quadrupole mass spectrometer equipped with the Finnigan Electrospray ionization system. Samples were prepared by reverse phase fractionation using a C4 column as described above. The DNase B proteins eluted at 65% Buffer B and were lyophilized for storage. Prior to injection at a flow rate of 1 μl/min, the samples were solubilized in acetonitrile-water-acetic acid (50:50:1).

The molecular weights determined by mass spectroscopic analysis are as follows: recombinant DNase B (Example 1)—25,549; Fraction I of purified natural DNase B—25,390; Fraction II of purified natural DNase B—25,397. These results are consistent with the nucleotide and amino acid sequencing results, which indicate that the recombinant DNase B has one additional amino acid at the amino terminus. The difference in molecular weights between Fractions I and II of the purified natural DNase B is consistent with a minor modification of an otherwise identical amino acid sequence. A possible modification is deamination, which would cause the appropriate pI shift.

Example 4

Purification and Amino-terminal Sequence Analysis of Recombinant *S. pyogenes* DNase B Produced From Bacteriophage λ2-6 Clone The recombinant DNase B protein in the λ DNase B 2-6 phage lysate was identified on an SDS-polyacrylamide gel by Western blot analysis. Rabbit antibody against commercial DNase B was used to detect the presence of recombinant DNase B. Only one protein band was detectable. Coomassie blue staining of an SDS-polyacrylamide gel suggests that the recombinant DNase B protein was about 5% of the total protein in the lysate. Only one nuclease was detected in a SDS-DNA-polyacrylamide gel system. The nuclease has a apparent molecular weight of 25,000 daltons.

The purification of the recombinant DNase B protein was monitored using SDS-polyacrylamide gel and a nuclease activity assay using the substrate used for a control in the commercial DNase B assay kit. The purification procedure included: (1) chromatography on Q-sepharose (trimethylaminomethyl agarose); (2) ammonium sulfate precipitation; (3) chromatography on heparin-agarose; and (4) chromatography on Q-sepharose. Two liters of a λ DNase B 2.6 phage lysate was prepared as an overnight culture on Luria broth supplemented with 10 mM MgCl$_2$. The supernatant was collected after centrifugation of the culture in a Beckman Instruments (Fullerton, Calif.) centrifuge at 3635× g at 4° C. for 45 minutes to remove cell debris (the volume of supernatant was 1900 ml).

The lysate was filtered through a 0.45 μm filtration unit to remove residual bacteria and cell debris. This filtrate was then passaged through an approximately 200-ml column of Q-sepharose (Pharmacia, Piscataway, N.J., which had been equilibrated with 20 mM Tris-HCl, pH 7.5, 1 mM EDTA. The flow-through from the column was collected. To this fraction, ammonium sulfate was added slowly to a final concentration of 80% at room temperature to concentrate the lysate. The desalted proteins were centrifuged at 15,000× g for 30 minutes.

Glycerol was added to the dialyzed proteins to a final concentration of 10%. This preparation was filtered through a 0.45 μm filtration unit. Conductivity of the protein preparation was determined, and the protein preparation was diluted with 20 mM Tris-HCl, pH 7.5, so that the conductivity was the same as that of a solution of 20 mM Tris-pH 7.5, 25 mM NaCl, 10% glycerol (Buffer A). The final volume was 1800 ml.

This sample was loaded on to a heparin-sepharose column (approximately 100 ml) on a Pharmacia FPLC system at a flow rate of 120 ml/hr. The column was washed with 400 ml of Buffer A. The DNase B was eluded with one liter of a gradient from 25 mM to 500 mM NaCl in Buffer A. The DNase activity eluted at approximately 125 mM NaCl in a volume of approximately 175 ml.

The DNase fraction eluted from the heparin agarose column was dialyzed against 20 mM Tris-HCl, pH 8.5, and was loaded on to an approximately 175-milliliter Q-sepharose column that had been equilibrated in 20 mM Tris-HCl, pH 8.5. The flow-through from the Q-sepharose column was collected and analyzed by isoelectric focusing activity gels, silver staining, and by SDS-polyacrylamide gel electrophoresis. The preparation of recombinant DNase B protein was 99% homogeneous. The protein concentration in the final eluate (110 ml) was about 100 μg/ml. This is equivalent to a yield of about 5.5 mg/liter of culture. The final product was then subjected to reverse phase high-pressure liquid chromatography, as described above in Example 3.

The amino-terminal sequence of purified recombinant DNase B was determined using a Beckman Microsequencing System 2020/Gold. The amino acid sequence was identical to that of natural *S. pyogenes* DNase B, except that the amino-terminus was arginine (R), and was R-Q-T-Q-V-S-N-D-V-V-L-N-D-G-A-S-K-Y-L-N-E-A-L-A-W-T-F-N-D-S-P-N-Y-Y-K-T-L-G (SEQ ID NO: 6). This arginine arose from the process of producing the recombinant DNase B.

Mass spectroscopic analysis of the DNase B showed that the DNase was homogeneous, with an apparent molecular weight of 25,549.

Example 5

Cloning and Expression of *S. pyogenes* DNase B Enzyme in an *Escherichia coli* Plasmid Under Regulation of the pL Promoter An additional genetic construction was made to demonstrate the regulated expression of the *S. pyogenes* DNase B gene using a plasmid vector incorporating the bacteriophage λ promoter pL. This construction was made by using the polymerase chain reaction (PCR) to incorporate modified ends to the DNase B gene in the λ 2-6 clone. The following oligonucleotides were designed and synthesized on the Pharmacia Gene Assembler Plus DNA synthesizer following the manufacturer's recommendations:

```
A: 5'-T-A-A-C-G-G-A-T-C-C-G-A-A-T-C-T-A-C-T-T-G-G-A-    (SEQ ID NO:2)
   T-C-A-A-G-A-C-G-G-G-T-T-T-T-T-C-T-3'

B: 3'-T-C-T-T-T-T-T-C-G-T-T-A-C-T-A-A-C-G-G-C-A-G-T-A-  (SEQ ID NO:3)
   A-C-G-G-G-G-C-C-A-G-C-T-G-G-G-C-C-5'
```

These oligonucleotides were used as primers in a PCR reaction using the AmpliTaq kit (Perkin-Elmer-Cetus, Norwalk, Conn.), according to the manufacturer's instructions. The final concentration of MgCl$_2$ was adjusted to 4 mM, and a 20 cycle reaction was performed (37° C., 2 minutes; 72° C., 3 minutes; 95° C., 2 minutes) using the Perkin-Elmer 480 thermal cycler. DNA of the λ gt11 clone 2-6 (100 ng) was used as a template along with 200 μM of each primer. The resulting amplified product was further digested with Bam HI and Sal I prior to insertion into the Δ33 expression vector. These manipulations created a translational fusion with the sequence as shown in FIG. 5, which is regulated by the λ pL promoter.

C 600 Cl$^+$, galK$^-$ bacteria were transformed with the ligation mixture and plated on to LB-Amp plates. Thereafter, a minipreparation of DNA was made (F. M. Ausubel et al., eds., "Current Protocols in Molecular Biology" (John Wiley, 1987), Section 1.6), followed by cutting the plasmid with the enzymes Bam HI and Sal I to determine if the plasmid comprised the recombinant DNase B fragment. Plasmids of the desired construction were further transformed into the AR120 host strain. These host cells with plasmids comprising the recombinant DNase B were then subjected to induction via the nalidixic acid protocol (Mott et al., supra). Colonies comprising the transformed AR120 were lifted from the agar plates and inoculated in Superbroth (base: 12 g tryptone, 24 g yeast extract, 5 ml glycerol, 900 ml distilled $H_2O$; salts per liter of base: 1.7 g $KH_2PO_4$, 15.8 g $K_2HPO_4$ (anhydrous), 100 ml distilled $H_2O$), plus 100 µg/ml ampicillin and grown at 37° C. until the optical density of the culture at 650 nm equalled 0.4.

Thereafter, nalidixic acid was added to the inoculated mixture at a final concentration of 60 µg/ml. The culture was incubated at 37° C. for about 8 hours or, alternatively, overnight (approximately 16 hours). All cell fractions were assayed for DNAse B activity including supernatant from the culture, sonicated cell pellets, and supernatants from the sonicated cell pellets.

For the overnight induction, DNAse B was secreted outside the *E. coli* cells. The 8-hour induction had most of the DNAse B secreted outside the cell, with approximately 30% inside, recovered in the sonicated supernatant. The quantities of DNAse B were great enough to be visualized by Coomassie brilliant blue stain on polyacrylamide gel electrophoresis.

Example 6

Purification of Recombinant *S. pyogenes* DNAse B Produced in *E. coli* Under Regulation of the PL Promoter A quantity (6 liters) of a recombinant DNAse B clone was grown in superbroth and induced overnight as described in Example 5. The supernatant was harvested and concentrated with a Pellicon concentrator using a 10K membrane; concentration yielded a volume of 600 ml.

The concentrated extract was dialyzed against heparin buffer A (20 mM HEPES, pH 7.9, 2 mM dithiothreitol, 10 mM Mg $Cl_2$, 0.2 mM EDTA, 0.1 M NaCl, 10% glycerol). The heparin column was loaded, run, and eluted as in Example 3.

The eluate from the heparin column was dialyzed in 20 mM ethanolamine, pH 8.5. Small quantities of extraneous proteins were absorbed from the DNAse B preparation by batch absorption onto Q-sepharose. A quantity of Q-sepharose (100 ml) was equilibrated with 20 nM ethanolamine, pH 8.5, and added to 100 ml of the heparin DNAse B fraction. The Q-sepharose was allowed to bind to the extract in a batch procedure for 20 minutes at 4° C. After binding, the Q-sepharose was filtered through a 0.45 µm filtration unit. The resin was finally washed with 50 ml of 20 mM ethanolamine, pH 8.5 for 20 minutes, prior to separation by centrifugation. The two eluates from this procedure were combined and analyzed by reverse phase chromatography, amino acid sequencing, and mass spectroscopic analysis. For reverse phase chromatography, 1 ml of the purified DNAse B was passed through a C4 column and eluted at 65% Buffer B in a volume of 1 ml. The same buffers were used as for the purification of the native DNAse B in Example 3.

The amino acid sequence was determined using a Beckman Microsequencing System 2020/Gold. The amino acid sequence was R-Q-T-Q-V-S-N-D-V-V-L-N-D-G-A-S-K-Y-L-N-E-A-L-A-W-T-F-N-D-S-P-N-Y-Y-K-T-L-G (SEQ ID NO: 6).

Mass spectroscopy analysis was also performed in the same manner as described for natural DNAse B, with an equivalent result.

Example 7

Preparation of DNA Probe Corresponding to Amino-terminal Sequence of DNase B Enzyme Using the codon usage for highly expressed genes in enteric bacteria on the VAX GCG program (Table 1), the following degenerate probe was prepared: C-A-P-U-A-C-N-C-A-R-T-N-W-S-N-A-A-Y-G-A-Y-G-T (SEQ ID NO: 5). In this sequence, R is a purine (i.e. A or G), Y is a pyrimidine (T or C), S is G or C, W is A or T, and N is any of the four common deoxyribonucleotides. This probe hybridized efficiently to λgt11 clone 2.6, confirming that the native DNase B protein was derived from the cloned gene.

Example 8

Inhibition of Recombinant DNase B by Anti-DNase B Antibody

Figure 6:
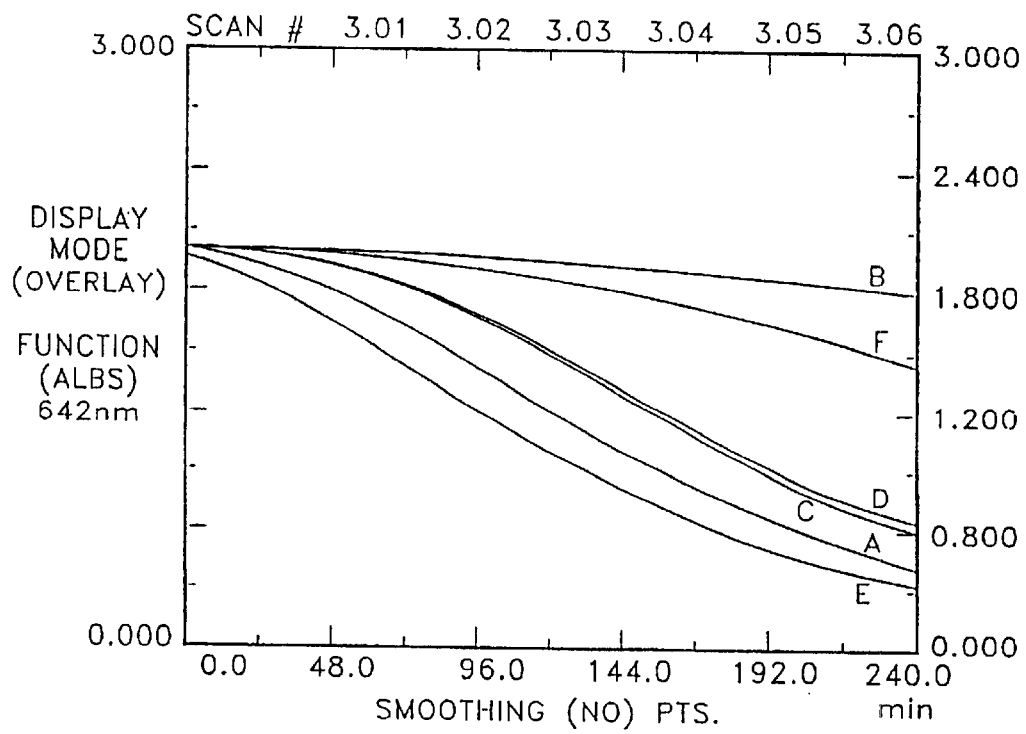

To show that the recombinant *S. pyogenes* DNase B is equivalent in its properties to natural DNase B, an immunoinhibition assay was performed. The recombinant DNase B was compared with commercially available natural DNase B in an inhibition assay using control positive human serum containing anti-DNase B antibody. The assay used was based on the ability of the DNase B to use a DNA-dye complex as substrate. This complex exhibits a maximum optical absorption at 642 nm. However, as the DNA-dye complex is degraded by the DNase, there is a shift in the maximum wavelength of absorption, and enzyme activity is indicated by a decrease in the measured absorption at 642 nm. As shown in FIG. 6, the recombinant enzyme is inactivated in an identical manner to the natural *S. pyogenes* DNase B by human serum containing anti-DNase B enzyme as the result of an immune reaction against naturally occurring *S. pyogenes* DNase B.

Example 9

Determination that Transcription of the DNase B Gene is Occurring from a Streptococcus Promoter in the Λ2-6 Clone As shown in Example 4, there was a high level of expression of the DNase B gene from the λ2-6 clone. In order to determine the start site of the strong bacterial promoter responsible for this expression, an in vitro runoff transcription assay was performed using *E. coli* RNA polymerase. This assay allows one to determine a precise base of transcriptional initiation by comparing the length of a transcriptional RNA runoff with a Sanger dideoxy sequencing ladder. This assay provides strong evidence for the start site of transcription in *E. coli*. Comparison with the known transcriptional start sites of a variety of Streptococcus further verifies this site to be the region responsible for streptococcal transcription (J. Ferretti & R. Curtiss, "Streptococcal Genetics" (1987), p. 293 ("Compilation of Nucleotide Sequences that Signal the Initiation of Transcription and Translation in Streptococci").

In a runoff transcription reaction, the RNA polymerase recognizes promoter regions and initiates transcription. The enzyme eventually falls off the end of the template, hence this is runoff transcription. This is a standard method for studying transcription start sites.

A PCR fragment which includes the upstream region of the DNase B gene was made as a template for an in vitro runoff transcription reaction with E. coli RNA polymerase. Using two oligonucleotides, oligonucleotide #246 at positions 298 to 280 and oligonucleotide #267 (not shown in FIG. 3), a PCR DNA product of approximately 290 base pairs was made and the fragment was purified after gel electrophoresis. The runoff transcription reaction was performed in 30 mM Tris pH 8, 120 mM KCl, 4 mM $MgCl_2$, 10 mM 2-mercaptoethanol, 4 mM spermidine, 0.4 mM ATP, 0.4 mM CTP, 0.4 mM GTP, 0.08 mM UTP, 80 units RNAsin (Promega), 1 unit RNA polymerase (Promega) and 5 µl [$^{32}$P] UTP in a total volume of 100 µl. The mixture was incubated at 37° C. for 30 minutes. In order to stop the reaction, 10 µl of 0.5 M EDTA was added.

The sample was diluted and electrophoresed on a sequencing gel. In order to accurately determine the size of the transcript, a sequencing reaction using oligonucleotide 246 on 2-6 DNA was performed. The reaction was done using the GIBCO/BRL (Bethesda, Md.) cycle sequencing kit. The starting point of the sequencing ladder is the same as the runoff point of the runoff transcript. By analyzing the transcription product along with the sequencing ladder in a urea polyacrylamide gel, the location of the transcription initiation site was determined.

FIG. 7 shows the DNA sequence upstream of the open reading frame and the consensus sequence of an E. coli promoter (D. K. Hawley & W. R. McClure, Nucl. Acids Res. 11:2237-2255 (1983)). The transcription data suggests that there are two possible start sites, position 96 and 97, for RNA polymerase. These sites are marked by an asterisk in FIG. 7. The −35 and −10 regions are underlined.

Example 10

Figure 8:
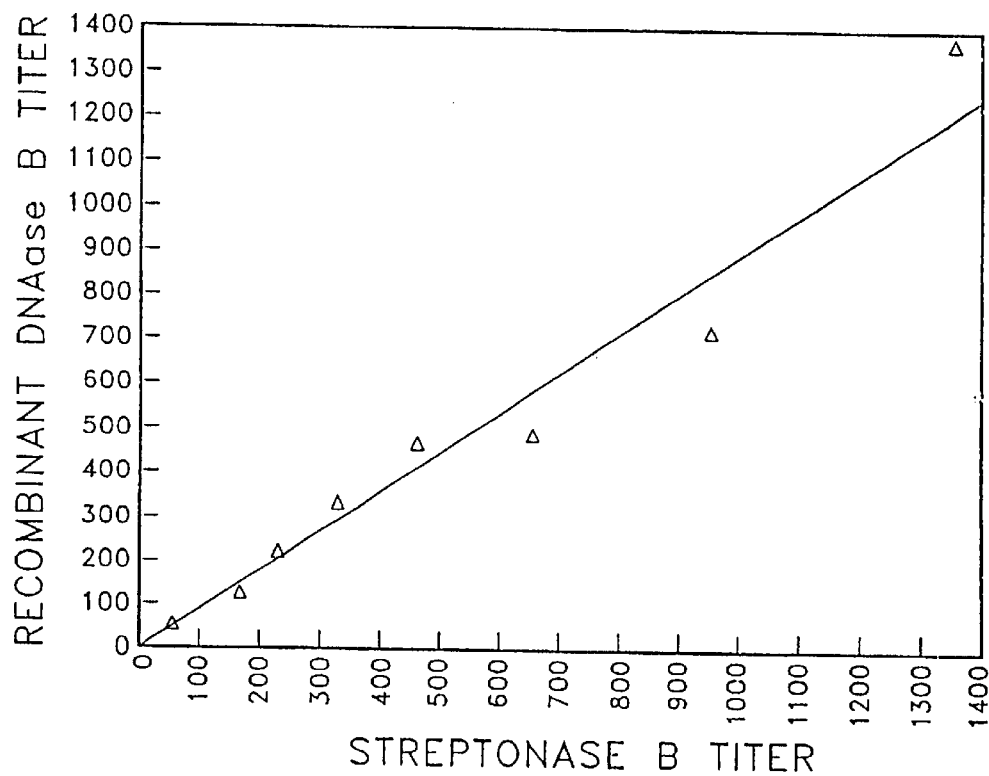

Equivalence of Purified Recombinant S. pyogenes DNAse B with Natural DNAse B in Reaction with Anti-DNAse Antibody in Human Serum Samples To show that recombinant DNAse B was substantially equivalent with natural DNAse B in the form of commercial Streptonase B, in their reaction with anti-DNAse antibody in human serum samples, the purified DNAse B enzyme was used in place of the commercial Streptonase B in the Streptonase B assay. Ten patient samples from Boston Biomedica (Boston, Mass.) were tested following the directions provided in the Streptonase B diagnostic kit. The same samples were also tested using purified recombinant DNAse B diluted to give similar nuclease activity as the reconstituted Streptonase B. The results are shown in Table 2 and graphed in the form of a correlation curve in FIG. 8.

TABLE 2

EQUIVALENCE OF RECOMBINANT DNase B WITH ISOLATED DNase B IN DETERMINATION OF ANTI-DNase B ANTIBODY TITER As can be seen, the correlation between the results using commercial Streptonase B and the purified recombinant DNAse is quite high. Thus, purified recombinant DNAse B reacts in substantially the same manner with anti-DNAse antibody found in serum as does commercial Streptonase B.

Example 11

Lack of Mitogenic Activity of Purified Natural DNase B

In order to determine whether the purified natural DNase B had mitogenic activity in a human lymphocyte mitogenic assay, various fractions of the purified natural S. pyogenes DNase B were tested in a mitogenic assay similar to the procedure used by T. Yutsudo et al., "A New Type of Mitogenic Factor Produced by Streptococcus pyogenes," FEBS Lett. 308: 30–34 (1992). For the testing of DNAse B for mitogenic activity, human lymphocytes were isolated using a Ficoll-Paque (Pharmacia) one-step gradient procedure performed as described by the manufacturer. Lymphocytes were plated in a microtiter plate (96 Wells) at a concentration of $10^5$ cells/well. After three days of growth in a humidified atmosphere: 37° C., 5% $CO_2$, with 1 µCi of tritiated thymidine (Amersham, Arlington Heights, Ill., at 1 mCi/ml) was added to each well. After an additional 24 hours of growth, the cells were transferred to glass tubes using 20 µl of 100 mM EDTA dissolved in MEM media with 10% fetal bovine serum. After washing the wells with an additional 200 µl of MEM with 10% fetal bovine serum, 500 µl of 10% trichloroacetic acid (TCA) was added to each glass tube in order to precipitate the incorporated tritiated thymidine. The TCA/cell mixture was allowed to incubate on ice for 20 minutes prior to filtration onto glass filters (Schleicher and Schuell, Keene, N.H.). The filters were further washed with 5% TCA and 100% ethanol prior to drying and counting by scintillation. Concanavalin A (1 µg/ml to 100 µg/ml, as indicated) was used as a positive control for mitogenic activity.

The results are shown in FIG. 9 for E. coli DNase I, the heparin-sepharose fraction of Example 3, purified Fractions I and II of Example 3, and the recombinant S. pyogenes DNase B of Example 3. The results indicate that both the purified Fractions I and II, as well as the recombinant DNase B, are substantially free of mitogenic activity. The heparin-sepharose fraction did have detectable mitogenic activity, which was removed by further purification. This indicates that any mitogenic activity resided not in the DNase B protein, but in one or more contaminants.

Example 12

Construction of a Vector Which Expresses DNase B in E. coli Which is Processed Identically to the Native DNase B The genetic construction described in Examples 5 and 6 produced a recombinant DNase B protein in E. coli which differed from the natural DNase B protein in that the protein was processed at an amino acid one amino acid up from the natural processing site. In order to produce a recombinant DNAse B in E. coli which was absolutely identical to the fully processed and natural DNase B, a genetic construction was made which deletes this "extra" arginine at amino acid 43 (Ala-Arg-Gln-Thr-Gln-Val). This construction was made by using the polymerase chain reaction (PCR) to incorporate modified ends to the DNAase B gene in the λ 2-6 clone. The following oligonucleotides were designed and synthesized on the Pharmacia Gene Assembler Plus DNA synthesizer following the manufacturer's recommendations:

A. 5'-A-G-G-C-A-A-T-G-G-A-T-C-C-G-A-A-C-C-T-G-C-T- (SEQ ID NO:12)
G-G-G-T-T-C-C-C-G-T-C-G-T-G-T-T-T-T-C-T-C-C-A-A-A-A-A-A-T-G-C-
C-G-T-C-T-G-G-T-T-A-A-A-T-T-C-T-C-C-A-T-G-G-T-T-G-C-T-C-T-G-G-
T-T-T-C-C-G-C-T-A-C-C-A-T-G-G-C-T-G-T-T-A-C-C-A-C-C-G-T-T-A-C-
C-C-T-G-G-A-A-A-A-C-A-C-C-G-C-T-C-T-G-G-C-T-C-A-G-A-C-A-C-A-G-
G-T-C-T-C-A-A-A-T-G-A-T-G-T-T-G-T-T-C-T-A-A-A-T-G-A-T-G-G-C-G-
C-A-A-G-C-3'

B. 3'-T-C-T-T-T-T-C-G-T-T-A-C-T-A-A-C-G-G-C-A-G-T-A- (SEQ ID NO:13)
A-C-G-G-G-G-C-C-C-A-G-C-T-G-G-G-C-C-5'

These oligonucleotides were used as primers in a PCR reaction using the AmpliTaq kit (Perkin-Elmer-Cetus, Norwalk, Conn.), according to the manufacturer's instructions. The final concentration of MgCl$_2$ was adjusted to 4 mM, and a 20 cycle reaction was performed (37° C., 2 minutes; 72° C., 3 minutes; 95° C., 2 minutes) using the Perkin-Elmer 480 thermal cycler. DNA of the λ gt11 clone 2-6 (100 ng) was used as a template along with 200 μM of each primer. The resulting amplified product was further digested with Bam HI and Sal I prior to insertion into the Δ33 expression vector. These manipulations created a translational fusion with the sequence as shown in FIG. 10 (SEQ ID NO: 14), which is regulated by the λ pL promoter.

C 600 Cl+, gal K– bacteria were transformed with the ligation mixture and plated on to LB– Amp plates. Thereafter, a minipreparation of DNA was made (F. M. Ausubel et al., eds., "Current Protocols in Molecular Biology" (John Wiley, 1987), Section 1.6), followed by cutting the plasmid with the enzymes Bam HI and Sal I to determine if the plasmid comprised the recombinant DNAse B fragment. Plasmids of the desired construction were further transformed into the AR 120 host strain. These host cells with plasmids comprising the recombinant DNAse B were then subjected to induction via the nalidixic acid protocol (Mott et al., supra). Colonies comprising the transformed AR120 were lifted from the agar plates and inoculated in Superbroth (base: 12 g yeast extract, 5 ml glycerol, 900 ml distilled H$_2$0; salts per liter of base: 1.7 g KH$_2$PO$_4$ and 15.8 g K$_2$HPO$_4$ anhydrous in 100 ml of deionized H$_2$O plus 100 μg/ml ampicillin) and grown at 37° C. until the optical density of the culture at 600 nm equalled 0.4.

Thereafter, nalidixic acid was added to the inoculated mixture at a final concentration of 60 μg/ml. The culture was incubated at 37° C. for about 8 hours or, alternatively, overnight (approximately 16 hours). All cell fractions were assayed for DNase B activity including supernatant from the culture, sonicated cell pellets, and supernatants from the sonicated cell pellets. For the overnight induction, DNase B was secreted outside the E. coli cell. Quantities of DNase B were enough to be visualized by Coomassie stain, on polyacrylamide gel electrophoresis (PAGE). An IEF (3–9) gel was run, and silver stained. Compared to the previous clone under the pL promoter, there was a clear shift of the pI to the more acidic side.

Example 13

Purification of the Arginine Deletion Construction and Amino Acid Sequence Analysis Growth and purification of the recombinant DNAse B clone described in Example 12 was performed as described in Example 6. The amino acid sequence was determined using a Beckman Microsequencing System 2020/Gold. The amino acid sequence was determined to be Q-T-Q-V-S-N-D-V-V-L-N-D-G-A-S-K-Y-L-N-E-A-L-A-W-T-F-N-D-S-P-N-Y (SEQ ID NO: 16). This sequence analysis demonstrates that the cleavage product of the arginine deleted construction is identical to the natural DNase B protein produced in *Streptococcus pyogenes*.

Example 14

Coupling of DNase B to Carboxylate Latex Particles

Prospective Example

Carboxylate latex particles (Interfacial Dynamics Corp.) are coupled to DNase B. The particles are described as high density carboxylate latex particles. The particles typically come in approximately 4% solids in surfactant-free distilled water. Both the 29 nm and the 17 nm diameter particles can be used.

Latex particles (5 ml) are diluted 2× with 0.1 M sodium bicarbonate buffer, pH 7.75. On ice, with stirring, the carboxyl groups of the latex particles are activated using a water-soluble carbodiimide, 1-ethyl-3-(3-dimethylaminopropyl) carbodiimide (EDAC). A 20 mg/ml EDAC solution is made and added to the latex particles to a final concentration of 10 mM with constant stirring. After the addition of EDAC, N-hydroxysuccinimide (NHS) (80 mg/ml solution) is added to a final concentration of 70 mM. The latex particle solution turns turbid after the coupling reagents are added. The solution is then stirred for 1 hour on ice.

The excess reagents are removed by centrifugation in a Beckman J2-21M, JA 20 rotor at 18,000 rpm for 30 minutes at 10° C. The supernatant is decanted. The latex particles are resuspended in 10 ml of phosphate buffered saline (PBS) containing. 1% Tween-20 and 5 mg/ml recombinant DNase B. Small clumps are dispersed with gentle sonication for approximately 1-2 minutes with a Heat Systems-Ultrasonics Inc. sonicator, model W-385. The setting is at 2 using a microtip. The reaction mixture is slightly agitated at room temperature from approximately 20 hours.

The unbound DNase B is removed by ultracentrifugation in a Beckman L8-70, Ti60 rotor, at 30,000 rpm for 30 minutes. The supernatant is removed. The latex particles are resuspended in 10 ml of PBS. Small clumps are dispersed by sonication at the same setting as above for approximately 1-2 minutes. The PBS is removed by ultracentrifugation as described above. The washed latex particles are resuspended in 10 mL PBS+0.01% sodium azide. Alternatively, unbound DNase B can be removed by size exclusion chromatography. The final DNase B latex particle stock (approximately 2%) is stored at 4° C. until further dilution for use in an assay.

ADVANTAGES OF THE INVENTION

The present invention provides a method of obtaining highly purified *S. pyogenes* DNase B enzyme without the necessity of growing large quantities of *S. pyogenes*, an expensive and risky process. The enzyme can be obtained without having to purify it from other proteins of *S. pyogenes*; rather, the enzyme can be purified from recombinant phage-infected *Escherichia coli* or from *E. coli* transfected with an appropriate expression vector. The expression vector can be chosen so as to optimize expression.

The *S. pyogenes* DNase B can then be used to assay for anti-DNase B antibody in serum in an assay specific for DNase B. In particular, the availability of purified DNase B makes possible the use of an ELISA assay using purified enzyme adsorbed to the solid phase, which is an assay suitable for wide use and easy and convenient to perform. The assay is also of high sensitivity and specificity. Such an assay is particularly suitable for clinical use in detecting *S. pyogenes* infection.

Although the present invention has been described in considerable detail with regard to certain preferred versions thereof, other versions are possible. Therefore, the spirit and scope of the appended claims should not be limited to the description of the preferred version contained herein.

We claim:

1. A method for detecting or determining anti-*Streptococcus pyogenes* DNase B antibody in a test sample, wherein said antibody inhibits *Streptococcus pyogenes* DNase B enzyme activity, comprising the steps of:
   (a) providing a test sample suspected of containing anti-*Streptococcus pyogenes* DNase B antibody;
   (b) adding a quantity of a *Streptococcus pyogenes* DNase B to the test sample, the quantity being sufficient to produce a detectable level of enzymatic activity in the absence of inhibition of the enzymatic activity by anti-DNase B antibody in the test sample, the DNase B added to the test sample produced by a process comprising:
      (i) culturing a bacterial host cell transformed with an expression vector comprising a DNA sequence comprising DNA encoding the amino acid sequence of *Streptococcus pyogenes* DNase B enzyme as shown in FIG. 4 (SEQ ID NO: 9);
      (ii) using the cultured bacterial host cell to express the DNase B enzyme; and
      (iii) purifying the enzyme from the cultured bacterial host cell, the purified enzyme being substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added; and
   (c) determining a level of DNase B enzyme in the test sample by performing a DNase B enzyme assay to detect or determine the anti-*Streptococcus pyogenes* antibody in the test sample.

2. A method for detecting or determining anti-*Streptococcus pyogenes* DNase B antibody in a test sample, wherein said antibody inhibits *Streptococcus pyogenes* DNase B enzyme activity, comprising the steps of:
   (a) providing a test sample suspected of containing anti-*Streptococcus pyogenes* DNase B antibody;
   (b) adding a quantity of a *Streptococcus pyogenes* DNase B to the test sample, the quantity being sufficient to produce a detectable level of enzymatic activity in the absence of inhibition of the enzymatic activity by anti-DNase B antibody in the test sample, the DNase B added to the test sample produced by a process comprising:
      (i) culturing a bacterial host cell transformed with an expression vector comprising a DNA sequence including therein the nucleotide sequence of *Streptococcus pyogenes* DNase B enzyme as shown in FIG. 3 (SEQ ID NO: 7);
      (ii) using the cultured bacterial host cell to express the DNase B enzyme; and
      (iii) purifying the enzyme from the cultured bacterial host cell, the purified enzyme being substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added; and
   (c) determining a level of DNase B enzyme in the test sample by performing a DNase B enzyme assay to detect or determine the anti-*Streptococcus pyogenes* antibody in the test sample.

3. A method for detecting or determining anti-*Streptococcus pyogenes* DNase B antibody in a test sample, wherein said antibody inhibits *Streptococcus pyogenes* DNase B enzyme activity, comprising the steps of:
   (a) providing a test sample suspected of containing anti-*Streptococcus pyogenes* DNase B antibody;
   (b) adding a quantity of substantially purified *Streptococcus pyogenes* DNase B enzyme to the test sample, the quantity being sufficient to produce a detectable level of enzymatic activity in the absence of inhibition of the enzymatic activity by anti-DNase B antibody in the test sample, the DNase B enzyme being substantially free of proteins other than (1) the *S. pyogenes* DNase B enzyme and (2) *S. pyogenes* DNase B enzyme fused at its amino terminus with a leader peptide, the substantially purified enzyme being substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added; and
   (c) determining a level of DNase B enzyme in the test sample by performing a DNase B enzyme assay to detect or determine the anti-*Streptococcus pyogenes* antibody in the test sample.

4. A method for detecting or determining anti-*Streptococcus pyogenes* DNase B antibody in a test sample, wherein said antibody inhibits *Streptococcus pyogenes* DNase B enzyme activity, comprising the steps of:
   (a) providing a test sample suspected of containing anti-*Streptococcus pyogenes* DNase B antibody;
   (b) adding a quantity of substantially purified *Streptococcus pyogenes* DNase B enzyme to the test sample, the quantity being sufficient to produce a detectable level of enzymatic activity in the absence of inhibition of the enzymatic activity by anti-DNase B antibody in the test sample, the DNase B enzyme being produced by a process comprising:
      (i) absorption to and elution from diethylaminoethyl cellulose to produce a first eluate;

(ii) chromatography of the first eluate on phenyl agarose to produce a second eluate;
(iii) chromatography of the second eluate on heparin agarose to produce a third eluate; and
(iv) chromatofocusing of the third eluate to produce substantially purified DNase B enzyme substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added; and (c) determining a level of DNase B enzyme in the test sample by performing a DNase B enzyme assay to detect or determine the anti-*Streptococcus pyogenes* antibody in the test sample.

5. A method for detecting or determining anti-*Streptococcus pyogenes* DNase B antibody in a test sample, comprising the steps of:
   (a) preparing a buffered solution of a DNase B produced by a process comprising:
      (i) culturing a bacterial host cell transformed with an expression vector comprising a DNA sequence comprising DNA encoding the amino acid sequence of *Streptococcus pyogenes* DNase B enzyme as shown in FIG. 4 (SEQ ID NO: 9);
      (ii) using the cultured bacterial host cell to express the DNase B enzyme; and
      (iii) purifying the enzyme from the cultured bacterial host cell, the purified enzyme being substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added;
   (b) reacting the buffered DNase B solution with a test sample suspected of containing anti-*Streptococcus pyogenes* DNase B antibody; and
   (c) detecting a reaction between the DNase B and the anti-DNase B antibody by observing or measuring a change in light absorption or light scattering in the solution.

6. A method for detecting or determining anti-*Streptococcus pyogenes* DNase B antibody in a test sample, comprising the steps of:
   (a) preparing a buffered solution of a DNase B produced by a process comprising:
      (i) culturing a bacterial host cell transformed with an expression vector comprising a DNA sequence including therein the nucleotide sequence of *Streptococcus pyogenes* DNase B enzyme as shown in FIG. 3 (SEQ ID NO: 7);
      (ii) using the cultured bacterial host cell to express the DNase B enzyme; and
      (iii) purifying the enzyme from the cultured bacterial host cell, the purified enzyme being substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added;
   (b) reacting the buffered DNase B solution with a test sample suspected of containing anti-*Streptococcus pyogenes* DNase B antibody; and
   (c) detecting a reaction between the DNase B and the anti-DNase B antibody by observing or measuring a change in light absorption or light scattering in the solution.

7. A method for detecting or determining anti-*Streptococcus pyogenes* DNase B antibody in a test sample, comprising the steps of:
   (a) preparing a buffered solution of a substantially purified DNase B enzyme, the DNase B enzyme being substantially free of proteins other than (1) the *S. pyogenes* DNase B enzyme and (2) *S. pyogenes* DNase B enzyme fused at its amino terminus with a leader peptide, the substantially purified enzyme being substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added;
   (b) reacting the buffered DNase B solution with a test sample suspected of containing anti-*Streptococcus pyogenes* DNase B antibody; and
   (c) detecting a reaction between the DNase B and the anti-DNase B antibody by observing or measuring a change in light absorption or light scattering in the solution.

8. A method for detecting or determining anti-*Streptococcus pyogenes* DNase B antibody in a test sample, comprising the steps of:
   (a) preparing a buffered solution of substantially purified DNase B enzyme, the DNase B enzyme being produced by a process comprising:
      (i) absorption to and elution from diethylaminoethyl cellulose to produce a first eluate;
      (ii) chromatography of the first eluate on phenyl agarose to produce a second eluate;
      (iii) chromatography of the second eluate on heparin agarose to produce a third eluate; and
      (iv) chromatofocusing of the third eluate to produce substantially purified DNase B enzyme substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added;
   (b) reacting the buffered DNase B solution with a test sample suspected of containing anti-*Streptococcus pyogenes* DNase B antibody; and
   (c) detecting a reaction between the DNase B and the anti-DNase B antibody by observing or measuring a change in light absorption or light scattering in the solution.

9. A method for detecting and/or determining anti-*Streptococcus pyogenes* DNase B antibody in a test sample, wherein said antibody inhibits *Streptococcus pyogenes* DNase B enzyme activity, comprising the steps of:
   (a) providing a test sample suspected of containing anti-*Streptococcus pyogenes* DNase B antibody;
   (b) adding a detectable quantity of a *Streptococcus pyogenes* DNase B enzyme to the test sample, the quantity being sufficient to produce a detectable level of enzymatic activity in the absence of inhibition of the enzymatic activity by anti-DNase B antibody in the test sample, the DNase B enzyme produced by the process of:

(i) culturing a bacterial host cell transformed with an expression vector comprising a DNA sequence that is substantially purified DNA comprising DNA encoding a *Streptococcus pyogenes* DNase B amino acid sequence selected from the group consisting of the amino acid sequence of: (1) *Streptococcus pyogenes* DNase B as shown in FIG. 4 (SEQ ID NO: 9); and (2) a *Streptococcus pyogenes* DNase B variant comprising the amino acid sequence shown in FIG. 4 (SEQ ID NO: 9) and having a deletion, insertion or substitution of one or more amino acids shown in FIG. 4 (SEQ ID NO: 9), wherein the variant is capable of being recognized and bound by anti-*Streptococcus pyogenes* DNase B antibody;

(ii) using the cultured bacterial host cell to express the DNase B enzyme; and (iii) purifying the enzyme from the cultured bacterial host cell; and (c) determining a level of activity of DNase B enzyme in the test sample by performing a DNase B enzyme assay to detect and/or determine the anti-*Streptococcus pyogenes* antibody in the test sample.

10. A method for detecting and/or determining anti-*Streptococcus pyogenes* DNase B antibody in a test sample, wherein said antibody inhibits *Streptococcus pyogenes* DNase B enzyme activity, comprising the steps of:

(a) providing a test sample suspected of containing anti-*Streptococcus pyogenes* DNase B antibody;

(b) adding a detectable quantity of a *Streptococcus pyogenes* DNase B enzyme to the test sample, the quantity being sufficient to produce a detectable level of enzymatic activity in the absence of inhibition of the enzymatic activity by anti-DNase B antibody in the test sample, the DNase B enzyme produced by the process of:

(i) culturing a bacterial host cell transformed with an expression vector comprising a DNA sequence that is the DNA having the nucleotide sequence of FIG. 3 (SEQ ID NO: 7);

(ii) using the cultured bacterial host cell to express the DNase B enzyme; and (iii) purifying the enzyme from the cultured bacterial host cell; and (c) determining a level of activity of DNase B enzyme in the test sample by performing a DNase B enzyme assay to detect and/or determine the anti-*Streptococcus pyogenes* antibody in the test sample.

11. A method for detecting or determining anti-*Streptococcus pyogenes* DNase B antibody in a test sample, comprising the steps of:

(a) preparing a buffered solution of a DNase B produced by a process comprising:

(i) culturing a bacterial host cell transformed with an expression vector comprising a DNA sequence that is substantially purified DNA comprising DNA encoding a *Streptococcus pyogenes* DNase B amino acid sequence selected from the group consisting of the amino acid sequence of: (1) *Streptococcus pyogenes* DNase B as shown in FIG. 4 (SEQ ID NO: 9); and (2) a *Streptococcus pyogenes* DNase B variant comprising the amino acid sequence shown in FIG. 4 (SEQ ID NO: 9) and having a deletion, insertion or substitution of one or more amino acids shown in FIG. 4 (SEQ ID NO: 9), wherein the variant is capable of being recognized and bound by anti-*Streptococcus pyogenes* DNase B antibody;

(ii) using the cultured bacterial host cell to express the DNase B enzyme; and (iii) purifying the enzyme from the cultured bacterial host cell, the purified enzyme being substantially free of mitogenic activity such that when added to a mitogenic assay with mammalian lymphocytes, the level of mitogenic activity observed in the purified DNase B enzyme is equivalent to the level of mitogenic activity observed in a control sample to which no DNAse B enzyme has been added;

(b) reacting the buffered DNase B solution with a test sample suspected of containing anti-*Streptococcus pyogenes* DNase B antibody; and (c) detecting a reaction between the DNase B and the anti-DNase B antibody by observing or measuring a change in light absorption or light scattering in the solution.

12. A method for detecting or determining anti-*Streptococcus pyogenes* DNAse B antibody in a test sample, comprising the steps of:

(a) preparing a buffered solution of a DNAse B produced by a process comprising:

(i) culturing a bacterial host cell transformed with an expression vector comprising a DNA sequence that is selected from the group consisting of: (1) the DNA having the nucleotide sequence of FIG. 3 (SEQ ID NO: 7), and (2) a *Streptococcus pyogenes* DNAse B variant comprising the polynucleotide sequence shown in FIG. 3 (SEQ ID NO: 7), the variant having a deletion, insertion or substitution of one or more nucleic acids shown in FIG. 3 (SEQ ID NO: 7), and wherein the variant encodes a *Streptococcus pyogenes* DNAse B capable of being recognized and bound by anti-*Streptococcus pyogenes* DNAse B antibody;

(ii) using the cultured bacterial host cell to express the DNAse B enzyme; and (iii) purifying the enzyme from the cultured bacterial host cell, the purified enzyme being substantially free of mitogenic activity such that when added to a mitogenic assay with mammalian lymphocytes, the level of mitogenic activity observed in the purified DNAse B enzyme is equivalent to the level of mitogenic activity observed in a control sample to which no DNAse B enzyme has been added;

(b) reacting the buffered DNAse B solution with a test sample suspected of containing anti-*Streptococcus pyogenes* DNAse B antibody; and (c) detecting a reaction between the DNAse B and the anti-DNAse B antibody by observing or measuring a change in light absorption or light scattering in the solution.

13. The method of claim 5, wherein the reaction between the DNase B and the anti-DNase B antibody is observed or measured by a change in light scattering.

14. The method of claim 13, wherein the change in light scattering is detected by nephelometry.

15. The method of claim 5, wherein the DNase B is coupled to a latex particle.

16. The method of claim 7, wherein the reaction between the DNase B and the anti-DNase B antibody is observed or measured by nephelometry.

17. The method of claim 7, wherein the DNase B is coupled to a latex particle.

18. The method of claim 11, wherein the reaction between the DNase B and the anti-DNase B antibody is observed or measured by nephelometry.

19. The method of claim 11, wherein the DNase B is coupled to a latex particle.

\* \* \* \* \*

```
                         SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
          (A) LENGTH: 43 amino acids
          (B) TYPE: amino acid
          (D) TOPOLOGY: linear (ii) MOLECULE TYPE: peptide (iii) HYPOTHETICAL: NO (v) FRAGMENT TYPE: N-terminal (vi) ORIGINAL SOURCE:
          (A) ORGANISM: Streptococcus pyogenes (xi) SEQUENCE DESCRIPTION: SEQ ID NO:1:

Met Asn Leu Leu Gly Ser Arg Arg Val Phe Ser Lys Lys Cys Arg Leu
1               5                  10                  15

Val Lys Phe Ser Met Val Ala Leu Val Ser Ala Thr Met Ala Val Thr
            20                  25                  30

Thr Val Thr Leu Glu Asn Thr Ala Leu Ala Arg
            35                  40

(2) INFORMATION FOR SEQ ID NO:2:

(i) SEQUENCE CHARACTERISTICS:
          (A) LENGTH: 41 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Synthetic DNA primer (xi) SEQUENCE DESCRIPTION: SEQ ID NO:2:
```

```
TAACGGATCC GAATCTACTT GGATCAAGAC GGGTTTTTTC T                      41

(2) INFORMATION FOR SEQ ID NO:3:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic DNA primer (xi) SEQUENCE DESCRIPTION: SEQ ID NO:3:

CCGGGTCGAC CCGGGGAATG ACGGCAATCA TTGCTTTTTC T                      41

(2) INFORMATION FOR SEQ ID NO:4:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Streptococcus pyogenes (xi) SEQUENCE DESCRIPTION: SEQ ID NO:4:

Gln Thr Gln Val Ser Asn Asp Val Val Leu Asn Asp Gly Ala Ser Xaa
1               5                   10                  15

Tyr Leu Asn Glu Ala Leu Ala
            20

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic probe (xi) SEQUENCE DESCRIPTION: SEQ ID NO:5:

CAUACNCART NWSNAAYGAY GT                                           22

(2) INFORMATION FOR SEQ ID NO:6:

(i) SEQUENCE CHARACTERISTICS:
        (A) LENGTH: 38 amino acids
        (B) TYPE: amino acid
        (D) TOPOLOGY: linear
```

-continued (ii) MOLECULE TYPE: peptide (iii) HYPOTHETICAL: NO (v) FRAGMENT TYPE: N-terminal (vi) ORIGINAL SOURCE:
             (A) ORGANISM: Streptococcus pyogenes (xi) SEQUENCE DESCRIPTION: SEQ ID NO:6:

Arg Gln Thr Gln Val Ser Asn Asp Val Val Leu Asn Asp Gly Ala Ser
1               5                  10                  15

Lys Tyr Leu Asn Glu Ala Leu Ala Trp Thr Phe Asn Asp Ser Pro Asn
            20                  25                  30

Tyr Tyr Lys Thr Leu Gly
        35

(2) INFORMATION FOR SEQ ID NO:7:

(i) SEQUENCE CHARACTERISTICS:
             (A) LENGTH: 1083 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes (ix) FEATURE:
             (A) NAME/KEY: CDS
             (B) LOCATION: 129..944

(xi) SEQUENCE DESCRIPTION: SEQ ID NO:7:

GACAACGCCT TCTTTTTTCT CCTTACTATC TCCTTTAATT TTCATATTTT TTAAAAAAAC          60

TATTGATAAA CTAGTTAAGT AAGCGTATAC TATGGTTAGT TAGCGAAATT AGAAAAGAGG         120

ACAAGCAT ATG AAT CTA CTT GGA TCA AGA CGG GTT TTT TCT AAA AAA TGT         170
         Met Asn Leu Leu Gly Ser Arg Arg Val Phe Ser Lys Lys Cys
           1               5                  10

CGG CTA GTA AAA TTT TCA ATG GTA GCT CTT GTA TCA GCC ACA ATG GCT          218
Arg Leu Val Lys Phe Ser Met Val Ala Leu Val Ser Ala Thr Met Ala
 15                  20                  25                  30

GTA ACA ACA GTC ACA CTT GAA AAT ACT GCA CTG GCA CGA CAA ACA CAG          266
Val Thr Thr Val Thr Leu Glu Asn Thr Ala Leu Ala Arg Gln Thr Gln
                 35                  40                  45

GTC TCA AAT GAT GTT GTT CTA AAT GAT GGC GCA AGC AAG TAC CTA AAC          314
Val Ser Asn Asp Val Val Leu Asn Asp Gly Ala Ser Lys Tyr Leu Asn
             50                  55                  60

GAA GCA TTA GCT TGG ACA TTC AAT GAC AGT CCT AAC TAT TAC AAA ACT          362
Glu Ala Leu Ala Trp Thr Phe Asn Asp Ser Pro Asn Tyr Tyr Lys Thr
         65                  70                  75

TTA GGT ACT AGT CAG ATT ACT CCA GCA CTC TTT CCT AAA GCA GGA GAT          410
Leu Gly Thr Ser Gln Ile Thr Pro Ala Leu Phe Pro Lys Ala Gly Asp
     80                  85                  90

ATT CTC TAT AGC AAA TTA GAT GAG TTA GGA AGG ACG CGT ACT GCT AGA          458
Ile Leu Tyr Ser Lys Leu Asp Glu Leu Gly Arg Thr Arg Thr Ala Arg
 95                 100                 105                 110

GGT ACA TTG ACT TAT GCC AAT GTT GAA GGT AGC TAC GGT GTT AGA CAA          506
Gly Thr Leu Thr Tyr Ala Asn Val Glu Gly Ser Tyr Gly Val Arg Gln

```
                115                 120                     125
TCT TTC GGT AAA AAT CAA AAC CCC GCA GGA TGG ACT GGA AAC CCT AAT        554
Ser Phe Gly Lys Asn Gln Asn Pro Ala Gly Trp Thr Gly Asn Pro Asn
            130                 135                 140

CAT GTC AAA TAT AAA ATT GAA TGG TTA AAT GGT CTA TCT TAT GTC GGA        602
His Val Lys Tyr Lys Ile Glu Trp Leu Asn Gly Leu Ser Tyr Val Gly
            145                 150                 155

GAT TTC TGG AAT AGA AGT CAT CTC ATT GCA GAT AGT CTC GGT GGA GAT        650
Asp Phe Trp Asn Arg Ser His Leu Ile Ala Asp Ser Leu Gly Gly Asp
        160                 165                 170

GCA CTC AGA GTC AAT GCC GTT ACA GGA ACA CGT ACC CAA AAT GTA GGA        698
Ala Leu Arg Val Asn Ala Val Thr Gly Thr Arg Thr Gln Asn Val Gly
175                 180                 185                 190

GGT CGT GAC CAA AAA GGC GGC ATG CGC TAT ACC GAA CAA AGA GCT CAA        746
Gly Arg Asp Gln Lys Gly Gly Met Arg Tyr Thr Glu Gln Arg Ala Gln
                195                 200                 205

GAA TGG TTA GAA GCA AAT CGT GAT GGC TAT CTT TAT TAT GAA GTC GCT        794
Glu Trp Leu Glu Ala Asn Arg Asp Gly Tyr Leu Tyr Tyr Glu Val Ala
            210                 215                 220

CCA ATC TAC AAC GCA GAC GAG TTG ATT CCA AGA GCT GTC GTG GTA TCA        842
Pro Ile Tyr Asn Ala Asp Glu Leu Ile Pro Arg Ala Val Val Val Ser
            225                 230                 235

ATG CAA TCT TCT GAT AAT ACC ATC AAC GAG AAA GTA TTA GTT TAC AAC        890
Met Gln Ser Ser Asp Asn Thr Ile Asn Glu Lys Val Leu Val Tyr Asn
        240                 245                 250

ACA GCT AAT GGC TAC ACC ATT AAC TAC CAT AAC GGT ACA CCT ACT CAA        938
Thr Ala Asn Gly Tyr Thr Ile Asn Tyr His Asn Gly Thr Pro Thr Gln
255                 260                 265                 270

AAA TAATACCAAA AGGCTAGACC TCTGCTCACT AGGCCTAGCT TTTTACATCA             991
Lys

AAAAAAGCAA TGACTATAGA AAGTAAAAAT ACTAGAAAAA GCAATGATTG CCGTCATTGC     1051

TTTTTATGAA TTTGTGCAAA AAGCAAAAAA GC                                   1083

(2) INFORMATION FOR SEQ ID NO:8:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:8:

Met Asn Leu Leu Gly Ser Arg Arg Val Phe Ser Lys Lys Cys Arg Leu
 1               5                  10                  15

Val Lys Phe Ser Met Val Ala Leu Val Ser Ala Thr Met Ala Val Thr
                20                  25                  30

Thr Val Thr Leu Glu Asn Thr Ala Leu Ala Arg Gln Thr Gln Val Ser
            35                  40                  45

Asn Asp Val Val Leu Asn Asp Gly Ala Ser Lys Tyr Leu Asn Glu Ala
        50                  55                  60

Leu Ala Trp Thr Phe Asn Asp Ser Pro Asn Tyr Tyr Lys Thr Leu Gly
65                  70                  75                  80

Thr Ser Gln Ile Thr Pro Ala Leu Phe Pro Lys Ala Gly Asp Ile Leu
                85                  90                  95

Tyr Ser Lys Leu Asp Glu Leu Gly Arg Thr Arg Thr Ala Arg Gly Thr
            100                 105                 110

Leu Thr Tyr Ala Asn Val Glu Gly Ser Tyr Gly Val Arg Gln Ser Phe
```

```
                115                 120                 125
Gly Lys Asn Gln Asn Pro Ala Gly Trp Thr Gly Asn Pro Asn His Val
        130                 135                 140

Lys Tyr Lys Ile Glu Trp Leu Asn Gly Leu Ser Tyr Val Gly Asp Phe
145                 150                 155                 160

Trp Asn Arg Ser His Leu Ile Ala Asp Ser Leu Gly Gly Asp Ala Leu
                165                 170                 175

Arg Val Asn Ala Val Thr Gly Thr Arg Thr Gln Asn Val Gly Gly Arg
            180                 185                 190

Asp Gln Lys Gly Gly Met Arg Tyr Thr Glu Gln Arg Ala Gln Glu Trp
        195                 200                 205

Leu Glu Ala Asn Arg Asp Gly Tyr Leu Tyr Tyr Glu Val Ala Pro Ile
    210                 215                 220

Tyr Asn Ala Asp Glu Leu Ile Pro Arg Ala Val Val Ser Met Gln
225                 230                 235                 240

Ser Ser Asp Asn Thr Ile Asn Glu Lys Val Leu Val Tyr Asn Thr Ala
                245                 250                 255

Asn Gly Tyr Thr Ile Asn Tyr His Asn Gly Thr Pro Thr Gln Lys
            260                 265                 270
```

(2) INFORMATION FOR SEQ ID NO:9:

(i) SEQUENCE CHARACTERISTICS:
        (A) LENGTH: 229 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Streptococcus pyogenes (xi) SEQUENCE DESCRIPTION: SEQ ID NO:9:

```
Arg Gln Thr Gln Val Ser Asn Asp Val Val Leu Asn Asp Gly Ala Ser
1               5                   10                  15

Lys Tyr Leu Asn Glu Ala Leu Ala Trp Thr Phe Asn Asp Ser Pro Asn
            20                  25                  30

Tyr Tyr Lys Thr Leu Gly Thr Ser Gln Ile Thr Pro Ala Leu Phe Pro
        35                  40                  45

Lys Ala Gly Asp Ile Leu Tyr Ser Lys Leu Asp Glu Leu Gly Arg Thr
    50                  55                  60

Arg Thr Ala Arg Gly Thr Leu Thr Tyr Ala Asn Val Glu Gly Ser Tyr
65                  70                  75                  80

Gly Val Arg Gln Ser Phe Gly Lys Asn Gln Asn Pro Ala Gly Trp Thr
                85                  90                  95

Gly Asn Pro Asn His Val Lys Tyr Lys Ile Glu Trp Leu Asn Gly Leu
            100                 105                 110

Ser Tyr Val Gly Asp Phe Trp Asn Arg Ser His Leu Ile Ala Asp Ser
        115                 120                 125

Leu Gly Gly Asp Ala Leu Arg Val Asn Ala Val Thr Gly Thr Arg Thr
    130                 135                 140

Gln Asn Val Gly Gly Arg Asp Gln Lys Gly Gly Met Arg Tyr Thr Glu
145                 150                 155

Gln Arg Ala Gln Glu Trp Leu Glu Ala Asn Arg Asp Gly Tyr Leu Tyr
```

```
                        165                 170                 175
Tyr Glu Val Ala Pro Ile Tyr Asn Ala Asp Glu Leu Ile Pro Arg Ala
                180                 185                 190

Val Val Val Ser Met Gln Ser Ser Asp Asn Thr Ile Asn Glu Lys Val
            195                 200                 205

Leu Val Tyr Asn Thr Ala Asn Gly Tyr Thr Ile Asn Tyr His Asn Gly
    210                 215                 220

Thr Pro Thr Gln Lys
225

(2) INFORMATION FOR SEQ ID NO:10:

(i) SEQUENCE CHARACTERISTICS:
        (A) LENGTH: 200 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (xi) SEQUENCE DESCRIPTION: SEQ ID NO:10:

GACAACGCCT TCTTTTTTCT CCTTACTATC TCCTTTAATT TTCATATTTT TTAAAAAAAC        60

TATTGATAAA CTAGTTAAGT AAGCGTATAC TATGGTTAGT TAGCGAAATT AGAAAAGAGG       120

ACAAGCATAT GAATCTACTT GGATCAAGAC GGGTTTTTTC TAAAAAATGT CGGCTAGTAA       180

AATTTTCAAT GGTAGCTCTT                                                   200

(2) INFORMATION FOR SEQ ID NO:11:

(i) SEQUENCE CHARACTERISTICS:
        (A) LENGTH: 940 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (xi) SEQUENCE DESCRIPTION: SEQ ID NO:11:

ATGGATCCGA ATCTACTTGG ATCAAGACGG GTTTTTTCTA AAAAATGTCG GCTAGTAAAA        60

TTTTCAATGG TAGCTCTTGT ATCAGCCACA ATGGCTGTAA CAACAGTCAC ACTTGAAAAT       120

ACTGCACTGG CACGACAAAC ACAGGTCTCA ATGATGTTG TTCTAAATGA TGGCGCAAGC        180

AAGTACCTAA ACGAAGCATT AGCTTGGACA TTCAATGACA GTCCTAACTA TTACAAAACT       240

TTAGGTACTA GTCAGATTAC TCCAGCACTC TTTCCTAAAG CAGGAGATAT TCTCTATAGC       300

AAATTAGATG AGTTAGGAAG GACGCGTACT GCTAGAGGTA CATTGACTTA TGCCAATGTT       360

GAAGGTAGCT ACGGTGTTAG ACAATCTTTC GGTAAAAATC AAAACCCCGC AGGATGGACT       420

GGAAACCCTA ATCATGTCAA ATATAAAATT GAATGGTAA ATGGTCTATC TTATGTCGGA        480

GATTTCTGGA ATAGAAGTCA TCTCATTGCA GATAGTCTCG GTGGAGATGC ACTCAGAGTC       540
```

```
AATGCCGTTA CAGGAACACG TACCCAAAAT GTAGGAGGTC GTGACCAAAA AGGCGGCATG        600

CGCTATACCG AACAAAGAGC TCAAGAATGG TTAGAAGCAA ATCGTGATGG CTATCTTTAT        660

TATGAAGTCG CTCCAATCTA CAACGCAGAC GAGTTGATTC CAAGAGCTGT CGTGGTATCA        720

ATGCAATCTT CTGATAATAC CATCAACGAG AAAGTATTAG TTTACAACAC AGCTAATGGC        780

TACACCATTA ACTACCATAA CGGTACACCT ACTCAAAAAT AATACCAAAA GGCTAGACCT        840

CTGCTCACTA GGCCTAGCTT TTTACATCAA AAAAAGCAAT GACTATAGAA AGTAAAAATA        900

CTAGAAAAAG CAATGATTGC CGTCATTGCC CCGGGTCGAC                              940

(2) INFORMATION FOR SEQ ID NO:12:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic primer (xi) SEQUENCE DESCRIPTION: SEQ ID NO:12:

AGGCAATGGA TCCGAACCTG CTGGGTTCCC GTCGTGTTTT CTCCAAAAAA TGCCGTCTGG         60

TTAAATTCTC CATGGTTGCT CTGGTTTCCG CTACCATGGC TGTTACCACC GTTACCCTGG        120

AAAACACCGC TCTGGCTCAG ACACAGGTCT CAAATGATGT TGTTCTAAAT GATGGCGCAA        180

GC                                                                      182

(2) INFORMATION FOR SEQ ID NO:13:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Synthetic primer (xi) SEQUENCE DESCRIPTION: SEQ ID NO:13:

CCGGGTCGAC CCGGGGCAAT GACGGCAATC ATTGCTTTTC T                            41

(2) INFORMATION FOR SEQ ID NO:14:

(i) SEQUENCE CHARACTERISTICS:
        (A) LENGTH: 937 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO
```

-continued (vi) ORIGINAL SOURCE:
    (A) ORGANISM: Streptococcus pyogenes (ix) FEATURE:
    (A) NAME/KEY: CDS
    (B) LOCATION: 1..819

(xi) SEQUENCE DESCRIPTION: SEQ ID NO:14:

| | | | | | | | | | | | | | | | | |
|---|---|---|---|---|---|---|---|---|---|---|---|---|---|---|---|---|
| ATG | GAT | CCG | AAC | CTG | CTG | GGT | TCC | CGT | CGT | GTT | TTC | TCC | AAA | AAA | TGC | 48 |
| Met | Asp | Pro | Asn | Leu | Leu | Gly | Ser | Arg | Arg | Val | Phe | Ser | Lys | Lys | Cys | |
| 1 | | | | 5 | | | | | 10 | | | | | 15 | | |
| CGT | CTG | GTT | AAA | TTC | TCC | ATG | GTT | GCT | CTG | GTT | TCC | GCT | ACC | ATG | GCT | 96 |
| Arg | Leu | Val | Lys | Phe | Ser | Met | Val | Ala | Leu | Val | Ser | Ala | Thr | Met | Ala | |
| | | | 20 | | | | | 25 | | | | | 30 | | | |
| GTT | ACC | ACC | GTT | ACC | CTG | GAA | AAC | ACC | GCT | CTG | GCT | CAG | ACA | CAG | GTC | 144 |
| Val | Thr | Thr | Val | Thr | Leu | Glu | Asn | Thr | Ala | Leu | Ala | Gln | Thr | Gln | Val | |
| | | 35 | | | | | 40 | | | | | 45 | | | | |
| TCA | AAT | GAT | GTT | GTT | CTA | AAT | GAT | GGC | GCA | AGC | AAG | TAC | CTA | AAC | GAA | 192 |
| Ser | Asn | Asp | Val | Val | Leu | Asn | Asp | Gly | Ala | Ser | Lys | Tyr | Leu | Asn | Glu | |
| 50 | | | | | 55 | | | | | 60 | | | | | | |
| GCA | TTA | GCT | TGG | ACA | TTC | AAT | GAC | AGT | CCT | AAC | TAT | TAC | AAA | ACT | TTA | 240 |
| Ala | Leu | Ala | Trp | Thr | Phe | Asn | Asp | Ser | Pro | Asn | Tyr | Tyr | Lys | Thr | Leu | |
| 65 | | | | | 70 | | | | | 75 | | | | | 80 | |
| GGT | ACT | AGT | CAG | ATT | ACT | CCA | GCA | CTC | TTT | CCT | AAA | GCA | GGA | GAT | ATT | 288 |
| Gly | Thr | Ser | Gln | Ile | Thr | Pro | Ala | Leu | Phe | Pro | Lys | Ala | Gly | Asp | Ile | |
| | | | | 85 | | | | | 90 | | | | | 95 | | |
| CTC | TAT | AGC | AAA | TTA | GAT | GAG | TTA | GGA | AGG | ACG | CGT | ACT | GCT | AGA | GGT | 336 |
| Leu | Tyr | Ser | Lys | Leu | Asp | Glu | Leu | Gly | Arg | Thr | Arg | Thr | Ala | Arg | Gly | |
| | | | 100 | | | | | 105 | | | | | 110 | | | |
| ACA | TTG | ACT | TAT | GCC | AAT | GTT | GAA | GGT | AGC | TAC | GGT | GTT | AGA | CAA | TCT | 384 |
| Thr | Leu | Thr | Tyr | Ala | Asn | Val | Glu | Gly | Ser | Tyr | Gly | Val | Arg | Gln | Ser | |
| | | 115 | | | | | 120 | | | | | 125 | | | | |
| TTC | GGT | AAA | AAT | CAA | AAC | CCC | GCA | GGA | TGG | ACT | GGA | AAC | CCT | AAT | CAT | 432 |
| Phe | Gly | Lys | Asn | Gln | Asn | Pro | Ala | Gly | Trp | Thr | Gly | Asn | Pro | Asn | His | |
| | 130 | | | | | 135 | | | | | 140 | | | | | |
| GTC | AAA | TAT | AAA | ATT | GAA | TGG | TTA | AAT | GGT | CTA | TCT | TAT | GTC | GGA | GAT | 480 |
| Val | Lys | Tyr | Lys | Ile | Glu | Trp | Leu | Asn | Gly | Leu | Ser | Tyr | Val | Gly | Asp | |
| 145 | | | | | 150 | | | | | 155 | | | | | 160 | |
| TTC | TGG | AAT | AGA | AGT | CAT | CTC | ATT | GCA | GAT | AGT | CTC | GGT | GGA | GAT | GCA | 528 |
| Phe | Trp | Asn | Arg | Ser | His | Leu | Ile | Ala | Asp | Ser | Leu | Gly | Gly | Asp | Ala | |
| | | | | 165 | | | | | 170 | | | | | 175 | | |
| CTC | AGA | GTC | AAT | GCC | GTT | ACA | GGA | ACA | CGT | ACC | CAA | AAT | GTA | GGA | GGT | 576 |
| Leu | Arg | Val | Asn | Ala | Val | Thr | Gly | Thr | Arg | Thr | Gln | Asn | Val | Gly | Gly | |
| | | | 180 | | | | | 185 | | | | | 190 | | | |
| CGT | GAC | CAA | AAA | GGC | GGC | ATG | CGC | TAT | ACC | GAA | CAA | AGA | GCT | CAA | GAA | 624 |
| Arg | Asp | Gln | Lys | Gly | Gly | Met | Arg | Tyr | Thr | Glu | Gln | Arg | Ala | Gln | Glu | |
| | | 195 | | | | | 200 | | | | | 205 | | | | |
| TGG | TTA | GAA | GCA | AAT | CGT | GAT | GGC | TAT | CTT | TAT | TAT | GAA | GTC | GCT | CCA | 672 |
| Trp | Leu | Glu | Ala | Asn | Arg | Asp | Gly | Tyr | Leu | Tyr | Tyr | Glu | Val | Ala | Pro | |
| | 210 | | | | | 215 | | | | | 220 | | | | | |
| ATC | TAC | AAC | GCA | GAC | GAG | TTG | ATT | CCA | AGA | GCT | GTC | GTG | GTA | TCA | ATG | 720 |
| Ile | Tyr | Asn | Ala | Asp | Glu | Leu | Ile | Pro | Arg | Ala | Val | Val | Val | Ser | Met | |
| 225 | | | | | 230 | | | | | 235 | | | | | 240 | |
| CAA | TCT | TCT | GAT | AAT | ACC | ATC | AAC | GAG | AAA | GTA | TTA | GTT | TAC | AAC | ACA | 768 |
| Gln | Ser | Ser | Asp | Asn | Thr | Ile | Asn | Glu | Lys | Val | Leu | Val | Tyr | Asn | Thr | |
| | | | | 245 | | | | | 250 | | | | | 255 | | |
| GCT | AAT | GGC | TAC | ACC | ATT | AAC | TAC | CAT | AAC | GGT | ACA | CCT | ACT | CAA | AAA | 816 |
| Ala | Asn | Gly | Tyr | Thr | Ile | Asn | Tyr | His | Asn | Gly | Thr | Pro | Thr | Gln | Lys | |
| | | | 260 | | | | | 265 | | | | | 270 | | | |

TAATACCAAA AGGCTAGACC TCTGCTCACT AGGCCTAGCT TTTTACATCA AAAAAGCAA    876

TGACTATAGA AAGTAAAAAT ACTAGAAAAA GCAATGATTG CCGTCATTGC CCCGGGTCGA    936

C                                                                   937

(2) INFORMATION FOR SEQ ID NO:15:

(i) SEQUENCE CHARACTERISTICS:
        (A) LENGTH: 272 amino acids
        (B) TYPE: amino acid
        (D) TOPOLOGY: linear (ii) MOLECULE TYPE: protein (xi) SEQUENCE DESCRIPTION: SEQ ID NO:15:

```
Met Asp Pro Asn Leu Leu Gly Ser Arg Arg Val Phe Ser Lys Lys Cys
  1               5                  10                  15

Arg Leu Val Lys Phe Ser Met Val Ala Leu Val Ser Ala Thr Met Ala
             20                  25                  30

Val Thr Thr Val Thr Leu Glu Asn Thr Ala Leu Ala Gln Thr Gln Val
         35                  40                  45

Ser Asn Asp Val Val Leu Asn Asp Gly Ala Ser Lys Tyr Leu Asn Glu
 50                  55                  60

Ala Leu Ala Trp Thr Phe Asn Asp Ser Pro Asn Tyr Tyr Lys Thr Leu
 65                  70                  75                  80

Gly Thr Ser Gln Ile Thr Pro Ala Leu Phe Pro Lys Ala Gly Asp Ile
                 85                  90                  95

Leu Tyr Ser Lys Leu Asp Glu Leu Gly Arg Thr Arg Thr Ala Arg Gly
            100                 105                 110

Thr Leu Thr Tyr Ala Asn Val Glu Gly Ser Tyr Gly Val Arg Gln Ser
        115                 120                 125

Phe Gly Lys Asn Gln Asn Pro Ala Gly Trp Thr Gly Asn Pro Asn His
130                 135                 140

Val Lys Tyr Lys Ile Glu Trp Leu Asn Gly Leu Ser Tyr Val Gly Asp
145                 150                 155                 160

Phe Trp Asn Arg Ser His Leu Ile Ala Asp Ser Leu Gly Gly Asp Ala
                165                 170                 175

Leu Arg Val Asn Ala Val Thr Gly Thr Arg Thr Gln Asn Val Gly Gly
            180                 185                 190

Arg Asp Gln Lys Gly Gly Met Arg Tyr Thr Glu Gln Arg Ala Gln Glu
        195                 200                 205

Trp Leu Glu Ala Asn Arg Asp Gly Tyr Leu Tyr Tyr Glu Val Ala Pro
210                 215                 220

Ile Tyr Asn Ala Asp Glu Leu Ile Pro Arg Ala Val Val Ser Met
225                 230                 235                 240

Gln Ser Ser Asp Asn Thr Ile Asn Glu Lys Val Leu Val Tyr Asn Thr
                245                 250                 255

Ala Asn Gly Tyr Thr Ile Asn Tyr His Asn Gly Thr Pro Thr Gln Lys
            260                 265                 270
```

(2) INFORMATION FOR SEQ ID NO:16:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (iii) HYPOTHETICAL: NO -continued

```
(vi) ORIGINAL SOURCE:
     (A) ORGANISM: Streptococcus pyogenes (xi) SEQUENCE DESCRIPTION: SEQ ID NO:16:

Gln Thr Gln Val Ser Asn Asp Val Val Leu Asn Asp Gly Ala Ser Lys
1               5                   10                  15

Tyr Leu Asn Glu Ala Leu Ala Trp Thr Phe Asn Asp Ser Pro Asn Tyr
            20                  25                  30
```